(12) United States Patent
Dvorkin et al.

(10) Patent No.: US 9,046,509 B2
(45) Date of Patent: Jun. 2, 2015

(54) METHOD AND SYSTEM FOR ESTIMATING ROCK PROPERTIES FROM ROCK SAMPLES USING DIGITAL ROCK PHYSICS IMAGING

(71) Applicant: Ingrain, Inc., Houston, TX (US)

(72) Inventors: Jack Dvorkin, Houston, TX (US); Naum Derzhi, Houston, TX (US)

(73) Assignee: Ingrain, Inc., Houston, TX (US)

( * ) Notice: Subject to any disclaimer, the term of this patent is extended or adjusted under 35 U.S.C. 154(b) by 110 days.

(21) Appl. No.: 13/895,454

(22) Filed: May 16, 2013

(65) Prior Publication Data

US 2013/0308831 A1 Nov. 21, 2013

Related U.S. Application Data

(60) Provisional application No. 61/649,099, filed on May 18, 2012.

(51) Int. Cl.
*G01N 33/24* (2006.01)
*E21B 47/00* (2012.01)
*G06T 7/00* (2006.01)

(52) U.S. Cl.
CPC .............. *G01N 33/24* (2013.01); *G01N 33/241* (2013.01); *E21B 47/00* (2013.01); *G06T 7/0004* (2013.01)

(58) Field of Classification Search
None
See application file for complete search history.

(56) References Cited

U.S. PATENT DOCUMENTS

| | | | |
|---|---|---|---|
| 6,516,080 B1 | 2/2003 | Nur | |
| 8,081,802 B2 * | 12/2011 | Dvorkin et al. | 382/109 |
| 8,590,382 B2 * | 11/2013 | Zaleski et al. | 73/606 |
| 8,805,616 B2 * | 8/2014 | Hinkel et al. | 702/11 |
| 8,838,428 B2 * | 9/2014 | Tapscott et al. | 703/10 |
| 2010/0135536 A1 * | 6/2010 | Dvorkin et al. | 382/109 |
| 2011/0066404 A1 * | 3/2011 | Salazar-Tio et al. | 703/1 |
| 2011/0295580 A1 | 12/2011 | Sisk et al. | |
| 2012/0275658 A1 * | 11/2012 | Hurley et al. | 382/109 |
| 2012/0277996 A1 * | 11/2012 | Hurley et al. | 702/11 |

(Continued)

OTHER PUBLICATIONS

International Search Report and Written Opinion for PCT/US2013/041276, Aug. 13, 2013.

(Continued)

*Primary Examiner* — Kim Vu
*Assistant Examiner* — Molly Delaney
(74) *Attorney, Agent, or Firm* — Kilyk & Bowersox, P.L.L.C.

(57) ABSTRACT

A method is provided for efficiently characterizing rock traversed while drilling a borehole for hydrocarbon reservoir development. A rock sample can be obtained having a provenance of collection linked to a specific region of the borehole, which is scanned to obtain a 2D digital image that is segmented to pixels characterized as pore space and as mineral matrix and defining a boundary between them. A transform relationship, for example, a form of the Kozeny-Carman equation adapted for application to a 2D segmented image environment, can be applied to calculate the estimated value for a target rock property, which can be absolute permeability, relative permeability, formation factor, elasticity, bulk modulus, shear modulus, compressional velocity, shear velocity, electrical resistivity, or capillary pressure, and the estimated value is used to characterize the rock at that region of the borehole. This affords an opportunity to quickly and efficiently develop massive data directly characterizing extended regions of rock, whether traversed by the borehole in this or a related well. Computerized systems, computer readable media, and programs for performing the methods are also provided.

28 Claims, 25 Drawing Sheets

(56) References Cited

U.S. PATENT DOCUMENTS

2013/0112605 A1* 5/2013 Wyndham et al. ......... 210/198.3
2014/0270394 A1* 9/2014 Fredrich et al. ............... 382/109

OTHER PUBLICATIONS

Schaap, M.G., et al., "Using microscope observations of thin sections to estimate soil permeability with the KozenyCarman equation," J. Hydrology, vol. 251, No. 3-4, 2001, pp. 186-201.

Lock, P.A., et al., "Predicting the permeability of sandstone from image analysis of pore structure," J. Applied Physics, New York, US, vol. 92, No. 10, Nov. 15, 2002, pp. 6311-6319.

Koplik, J., et al., "Conductivity and permeability from microgeometry," J. Applied Physics, vol. 56, No. 11, Dec. 1, 1984, pp. 3127-3131.

Dvorkin, J., et al., "From micro to reservoir scale: Permeability from digital experiments," The Leading Edge, vol. 28, No. 12, Dec. 2009, pp. 1446-1448 and 1450-1453.

Jurgawczynski, M., et al., "Estimating the Permeability of Carbonate Rocks Using Image Analysis and Effective Medium Theory," International Symposium of the Society of Core Analysts, Abu Dhabi, UEA, Oct. 5-9, 2004, SCA2004-37, pp. 1-11.

Tölke, J., et al., "Computer Simulations of fluid flow in sediment: From images to permeability," The Leading Edge, Jan. 2010, pp. 68-70 and 72-74.

Dvorkin, J., et al., "Relevance of computational rock physics," Geophysics, vol. 76, No. 5, Sep.-Oct. 2011, pp. E141-E153.

Mavko, G., et al., The Rock Physics Handbook: Tools for Seismic Analysis of Porous Media, Cambridge University Press, 2009, pp. 401-406.

Berryman, J.G., et al., "Elastic wave propagation in fluid-saturated porous media," Journal of the Acoustical Society of America, vol. 69, No. 2, Feb. 1981, pp. 416-424.

Boving, T.B., et al., "Tracer diffusion coefficients in sedimentary rocks: correlation to porosity and hydraulic conductivity," Journal of Contaminant Hydrology, vol. 53, 2001, pp. 85-100.

Mavko, G., et al., "The effect of a percolation threshold in the Kozeny-Carman relation," Geophysics, vol. 62, No. 5, Sep.-Oct. 1997, pp. 1480-1482.

Archie, G.E., "The Electrical Resistivity Log as an Aid in Determining Some Reservoir Characteristics," Petroleum Transactions of the AIME, 146, 1942, pp. 54-62.

* cited by examiner

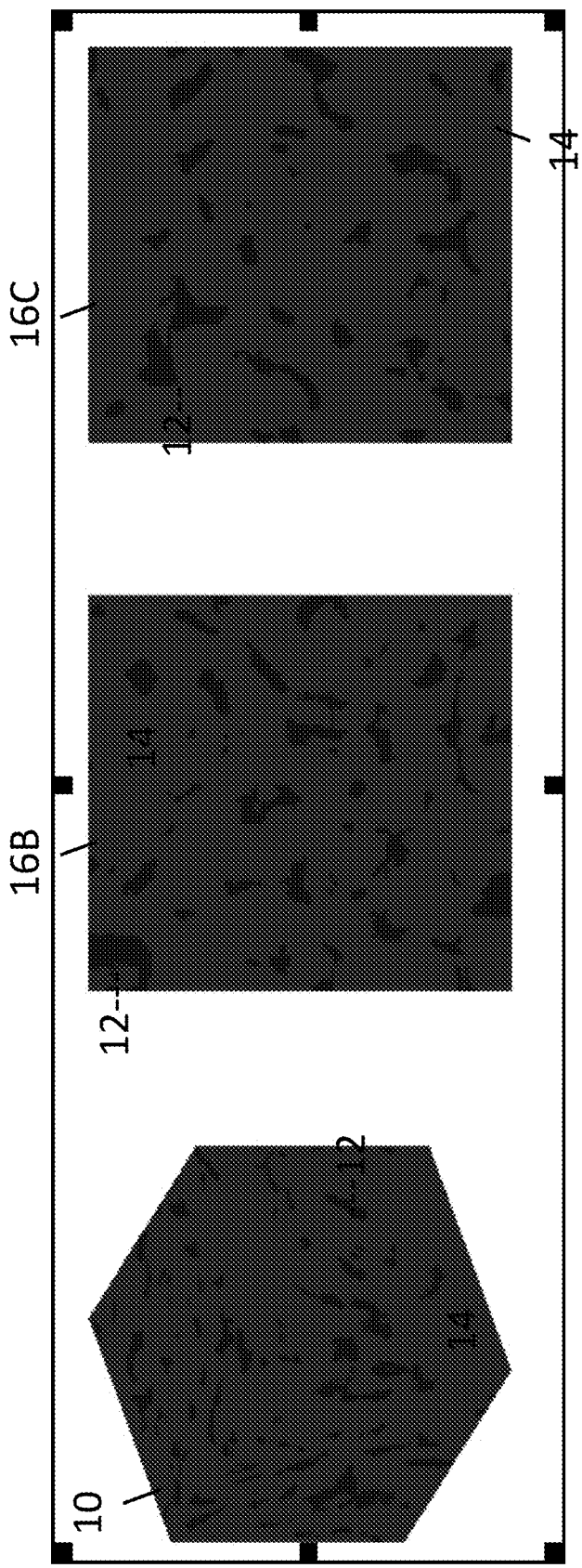

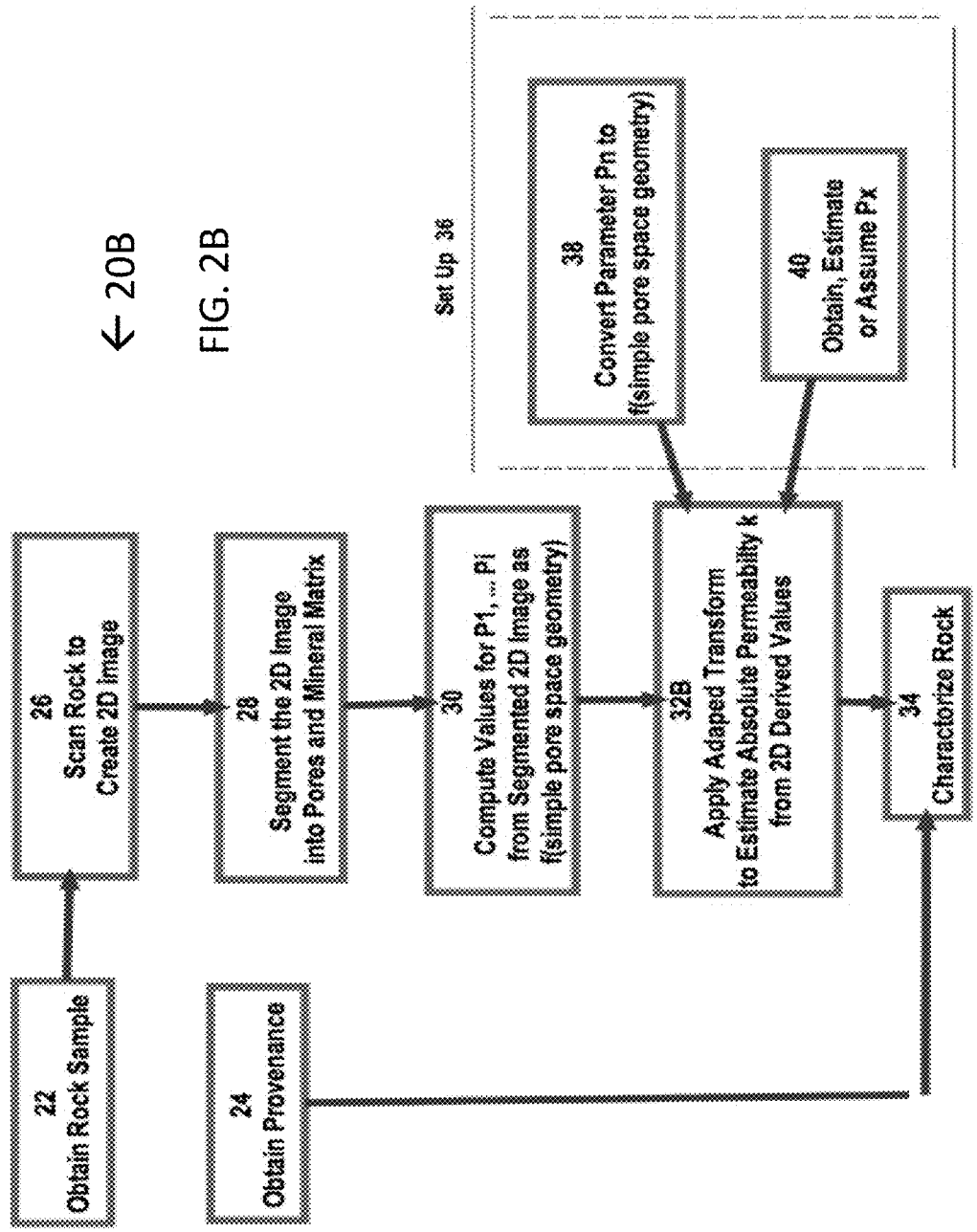

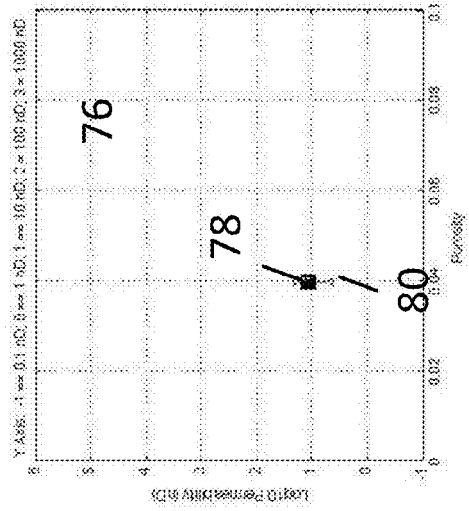
FIG. 13C
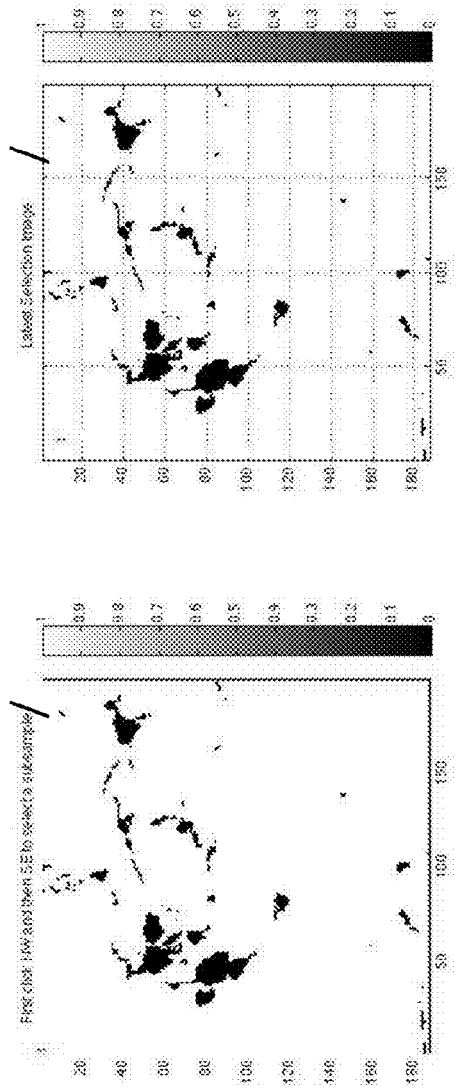
FIG. 13B
FIG. 13A
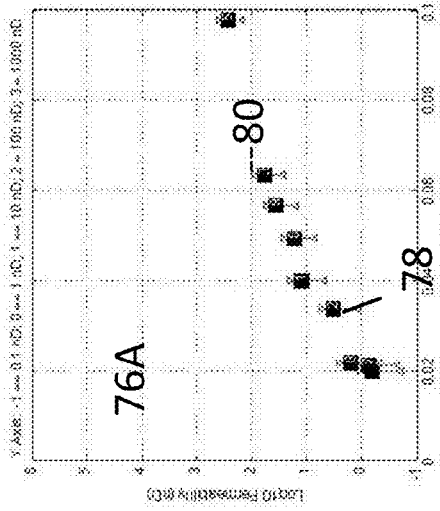
FIG. 13F
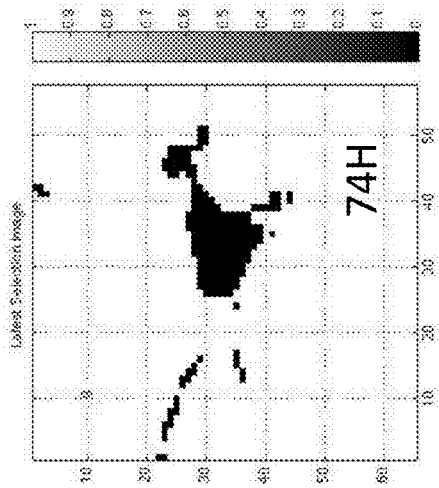
FIG. 13E
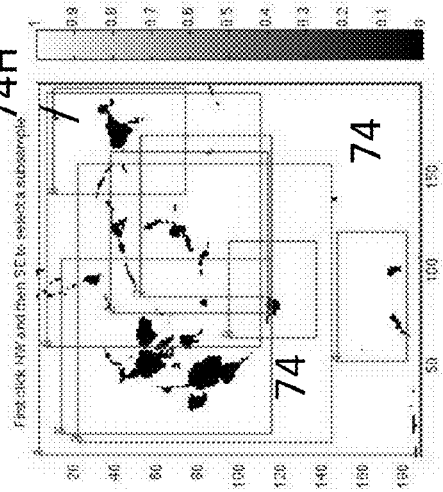
FIG. 13D

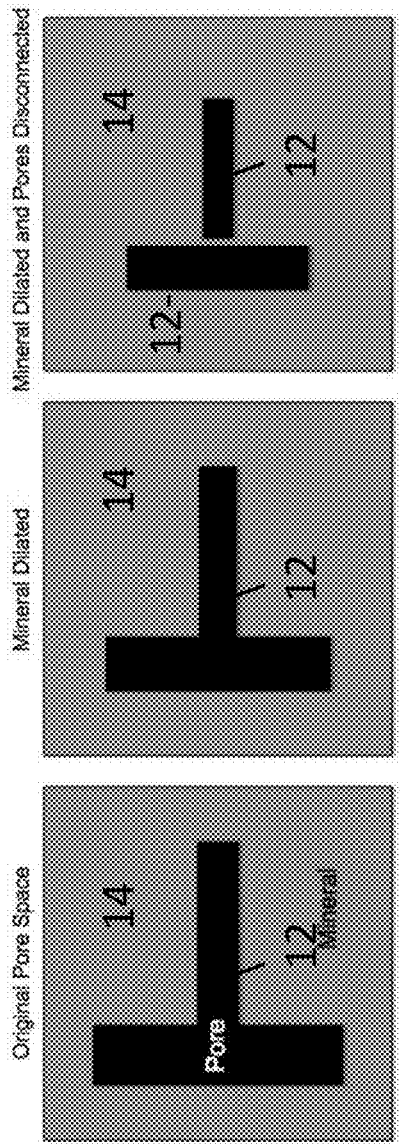

METHOD AND SYSTEM FOR ESTIMATING ROCK PROPERTIES FROM ROCK SAMPLES USING DIGITAL ROCK PHYSICS IMAGING

This application claims the benefit under 35 U.S.C. §119 (e) of prior U.S. Provisional Patent Application No. 61/649,099, filed May 18, 2012, which is incorporated in its entirety by reference herein.

BACKGROUND OF THE INVENTION

The invention relates generally to the field of digital rock physics and, more particularly, to a method for estimating rock property values, such as one or more of absolute permeability, relative permeability, formation factor, elasticity, and capillary pressure values, using digital rock physics techniques suitable for application to small scale rock samples such as cuttings returned to the surface in normal drilling operations, or other porous media, and applications where requirements for speed and volume otherwise may not be optimally met by 3D volume analysis.

An understanding of complex properties, such as absolute permeability, can be crucial to understanding the mobility of hydrocarbons in subsurface rock. This has implications for understanding the historic migration of oil to traps over geologic time as well as immediate commercial implications on well planning, completion design and reservoir estimates.

Traditionally, absolute permeability, for example, has been determined with a permeameter forcing a fluid through a rock sample and recording the resulting fluid flux and pressure drops. However, such attempts to acquire information are substantially constrained by the shape and size of the sample and are often otherwise not well suited to providing quality information in a timely manner.

Digital rock physics offers some of the most efficient opportunities for effectively characterizing the structure and composition of rock samples. Digital images of natural rock samples (typically, cores) can be obtained with X-Ray computed tomography scans (CT scans), focused ion beam scanning electron microscope (FIB-SEM scanning), magnetic resonance imaging, or other imaging techniques generally capable of useful resolution and digitization, including magnetic resonance imaging and other applications of microtomography or microradiography technology.

The type of sample preparation can depend upon the image capture method to be used and the type of image scanning instrument to be used. For example, rock samples can be cleaned, shaped, mounted, or otherwise prepared for image capture. Such preparation might, e.g., comprise cutting, abrading, shaping milling, focused ion beam polishing, other techniques to alter the size and shape of rocks, or any combinations thereof appropriate to ensure that the physical sample fits inside the field of view of the scanner and does not move during the scan.

These 3D volumes can be segmented through techniques discussed, e.g., in Toelke, J., et al. (2010), "Computer simulations of fluid flow in sediment: From images to permeability," The Leading Edge (January 2010), 68-74 (hereinafter, the "Toelke (2010)" publication), and U.S. Pat. No. 8,081,802 B2 to Dvorkin et al. (hereinafter, the '802 patent).

Values for important properties can then be estimated, modeled, or simulated with the resulting 3D segmented volumes, see, e.g., Dvorkin, J., et al. (2011), "Relevance of computation rock physics," Geophysics, 76(5), E141-E153 (hereinafter, the "Dvorkin 2011" publication). Toelke (2010) discusses the application of a Lattice-Bolzmann solution to Navier-Stokes equations (i.e., the Lattice-Bolzmann Method or "LBM") as the 3D analytic solution for absolute permeability k. The LBM solution models momentum of particles in movement through 3D space and requires a 3D volumetric analysis.

A possible limitation to the application of 3D scanning to drill cuttings is that it is not uncommon for many of the drill cuttings to be unsuitable in size for direct 3D scanning. And, depending upon the formation and specifics of the drilling program, there can be times when a great percentage of cuttings circulated to the surface will present challenges for a direct 3D investigation. In addition, the present inventors have recognized that there are situations for which an estimate of one or more of absolute permeability, relative permeability, formation factor, elasticity, and capillary pressure, would be very useful, but for which even the speed and efficiency attendant digital rock physics applied in current segmented volume analysis proves sub-optimal given the speed, efficiency and sheer massiveness desired for the data acquisition. Further, while there are a number of imaging devices, FIB-SEM is one of the most popular and easily available for applications in digital rock physics. And this technology, in particular, can be burdened by the foregoing challenges.

U.S. Pat. No. 6,516,080 to Nur et al. discloses use of 2D images to construct a simulated 3D segmented volume. Nevertheless, applications overserved by 3D investigations can be hindered by additional processes necessary to synthesize the 3D segmented volume before analysis can begin. In this regard, Nur et al.'s use of 2-D images to construct simulated 3D volumes is consistent with prior thinking that construction of a 3-D image of rock is essential for computing some complex rock properties such as permeability.

The present investigators have recognized that there remains a need for a very efficient process to obtain quality estimates of fluid transport properties, such as one or more of absolute permeability, relative permeability, formation factor, elasticity, and capillary pressure, from common sample sources, such as drill cuttings, and to apply digital rock physics without the rigors of creating, synthesizing, or otherwise obtaining 3D volumes. The present investigators have further recognized that such capabilities would afford important new opportunities to gather and use absolute permeability estimates characterizing a more complete collection of strata within a given well and from multiple strata from adjacent wells or otherwise identified with the same trend. Further, requirements of speed and efficiency suggest a preference for a very robust process that is applicable to a wide range of rocks so as to minimize calibration efforts where practical.

SUMMARY OF THE INVENTION

A feature of the present invention is a method for estimating a target rock property, such as absolute permeability, relative permeability, formation factor, elasticity, bulk modulus, shear modulus, elastic-wave velocities, electrical resistivity, or capillary pressure, of a rock sample for application of digital rock physics using two-dimensional (2D) images.

Another feature of the present invention addresses a method for efficiently characterizing rock traversed while drilling a borehole for hydrocarbon reservoir development with an estimated value for a target rock property, such as absolute permeability, relative permeability, formation factor, elasticity, bulk modulus, shear modulus, elastic-wave velocities, electrical resistivity, or capillary pressure.

To achieve these and other advantages and in accordance with the purposes of the present invention, as embodied and broadly described herein, the present invention relates, in part, to a method for estimating a target rock property of a rock sample from an application of digital rock physics in 2D, which comprises the steps of scanning a rock sample to obtain a 2D digital image of the rock sample; segmenting the digital image to produce a digital 2D segmented image having pixels characterized as pore space and pixels characterized as mineral matrix and defining a boundary at the intersection of pore space and the mineral matrix; deriving values for rock properties $P_1$-$P_i$ from the segmented image as a function of simple pore space geometry; and applying a transform relationship adapted for application to a 2D segmented image environment to calculate an estimated value for the target rock property as a function of simple pore space geometry derived from the 2D segmented image.

The present invention also relates to a method for efficiently characterizing rock traversed while drilling a borehole for hydrocarbon reservoir development with an estimated value for a target rock property comprising the steps of obtaining a rock sample having a provenance of collection linked to a specific region of the borehole; scanning the rock sample to obtain a 2D digital image of the rock sample; segmenting the digital image to produce a 2D segmented image having pixels characterized as pore space and pixels characterized as mineral matrix and defining a boundary at the intersection of pore space and mineral matrix; applying a transform relationship adapted for direct application to a 2D segmented image environment to calculate the estimated value for the target rock property; and using the estimated value for the target rock property directly derived from the 2D segmented image to characterize the rock at region of the borehole.

The present invention also relates to a method for efficiently characterizing rock traversed while drilling a borehole for hydrocarbon reservoir development with an estimated absolute permeability value k, comprising the steps of obtaining a rock sample having a provenance of collection linked to a specific region of the borehole; scanning the rock sample to obtain a 2D digital image of the rock sample, the scanning comprising using one or more scanning systems of a group comprising: focused ion beam scanning electron microscope; x-ray tomography; synchrotron, microtomography, and microradiology; segmenting the digital image to produce a 2D segmented image having pixels characterized as pore space and pixels characterized as solid matrix and defining a boundary at the intersection of pore space and solid matrix; applying a Kozeny-Carman equation adapted for direct application to a 2D segmented image environment with which an estimate is directly calculated from the 2D segmented image for absolute permeability; and using the estimate for absolute permeability calculated from the 2D segmented image to characterize the rock at the location in the borehole.

The present invention also relates to method for efficiently characterizing rock traversed while drilling a borehole for hydrocarbon reservoir development with an estimated absolute permeability value k, comprising the steps of obtaining a rock sample having a provenance of collection linked to a specific region of the borehole; scanning the rock sample to obtain a 2D digital image of the rock sample, the scanning comprising using one or more scanning systems of a group comprising: focused ion beam scanning electron microscope; x-ray tomography; synchrotron, microtomography, and microradiology; segmenting the digital image to produce a 2D segmented image having pixels characterized as pore space and pixels characterized as solid matrix and defining a boundary at the intersection of pore space and solid matrix; applying Timur's equation adapted for direct application to a 2D segmented image environment with which an estimate is directly calculated from the 2D segmented image for absolute permeability; and using the estimate for absolute permeability calculated from the 2D segmented image to characterize the rock at the location in the borehole.

The present invention also relates to a method for efficiently estimating absolute permeability k of rock traversed while drilling a borehole for hydrocarbon reservoir development, comprising the steps of obtaining a plurality of rock samples, each having a provenance of collection linked to a specific region of the borehole, the obtaining further comprising using rock samples collected from drill cuttings from drilling operations and associating the drill cutting to an axial depth in the borehole; scanning the rock sample to obtain a 2D digital image of the rock sample; segmenting the digital image to produce a 2D segmented image having pixels characterized as pore space and pixels characterized as solid matrix and defining a boundary at the intersection of pore space and solid matrix; estimating porosity $\phi$ as the number of pore space pixels divided by the total number of pixels in the 2D segmented image; estimating specific surface area s as the length of the boundary at the intersection of pore space and solid matrix divided by the area of the 2D segmented image; estimating a lower bound for absolute permeability $k_-$ according to the following relationship: $k_-=2.4957(\phi^{5.4}/s^2)$; estimating an upper bound for absolute permeability $k_+$ according to the following relationship: $k_+=3.0665\,[\phi^5/s^2(1+\phi)^2]$; and using the lower and upper bound estimates for absolute permeability calculated from the 2D segmented image to characterize the rock at the location in the boreholes.

Computerized systems, computer readable media, and programs for performing the methods are also provided.

Additional features and advantages of the present invention will be set forth in part in the description that follows, and in part will be apparent from the description, or can be learned by practice of the invention. The features and other advantages of the present invention will be realized and attained by means of the elements and combinations particularly pointed out in the description and appended claims.

It is to be understood that both the foregoing general description and following detailed description are exemplary and explanatory only and are intended to provide a further explanation of the present invention, as claimed.

A BRIEF DESCRIPTION OF THE DRAWINGS

The accompanying drawings, which are incorporated in and constitute a part of this application, illustrate features of the present invention and, together with the description, serve to explain the principles of the present invention. The same items in different figures are designated with the identical reference numerals and related items are often designated with the same reference numerals with a letter suffix appended.

FIG. 1A is a 3D image, a digital segmented volume representative of a rock sample;

FIG. 1B is a 2D segmented image corresponding to the same rock sample;

FIG. 1C is another 2D segmented image corresponding to the same rock sample;

FIG. 2B is a flow diagram illustrating a work flow in accordance with an illustrative example of the present application directed to estimating absolute permeability;

FIG. 13A illustrates an original 2D segmented image of another sample according to an example of the present application;

FIG. 13B illustrates the selection of a first investigation sample comprising substantially all of the original 2D segmented image of FIG. 13A according to an example of the present application;

FIG. 13C illustrates a graph of absolute permeability to porosity for the first investigation sample according to an example of the present application;

FIG. 13D illustrates a plurality of investigation subsamples defined in the segmented image of FIG. 13A according to an example of the present application;

FIG. 13E illustrates one of the investigation subsamples set out in FIG. 13D according to an example of the present application;

FIG. 13F is a graph of permeability against porosity illustrating a permeability trend from investigation samples and subsamples identified in FIGS. 13B, 13D and 13E according to an example of the present application;

Figure 15:
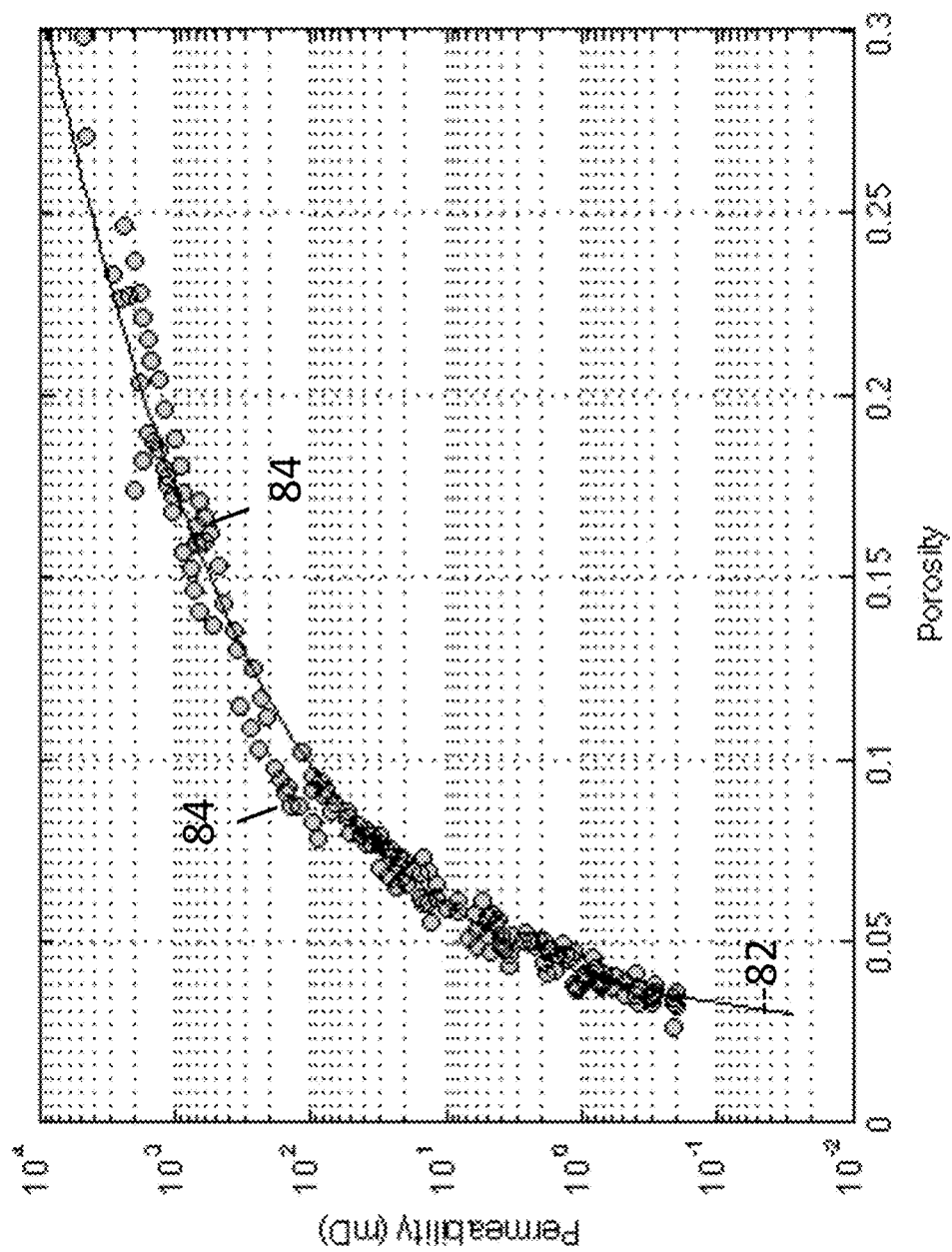
Figure 16:
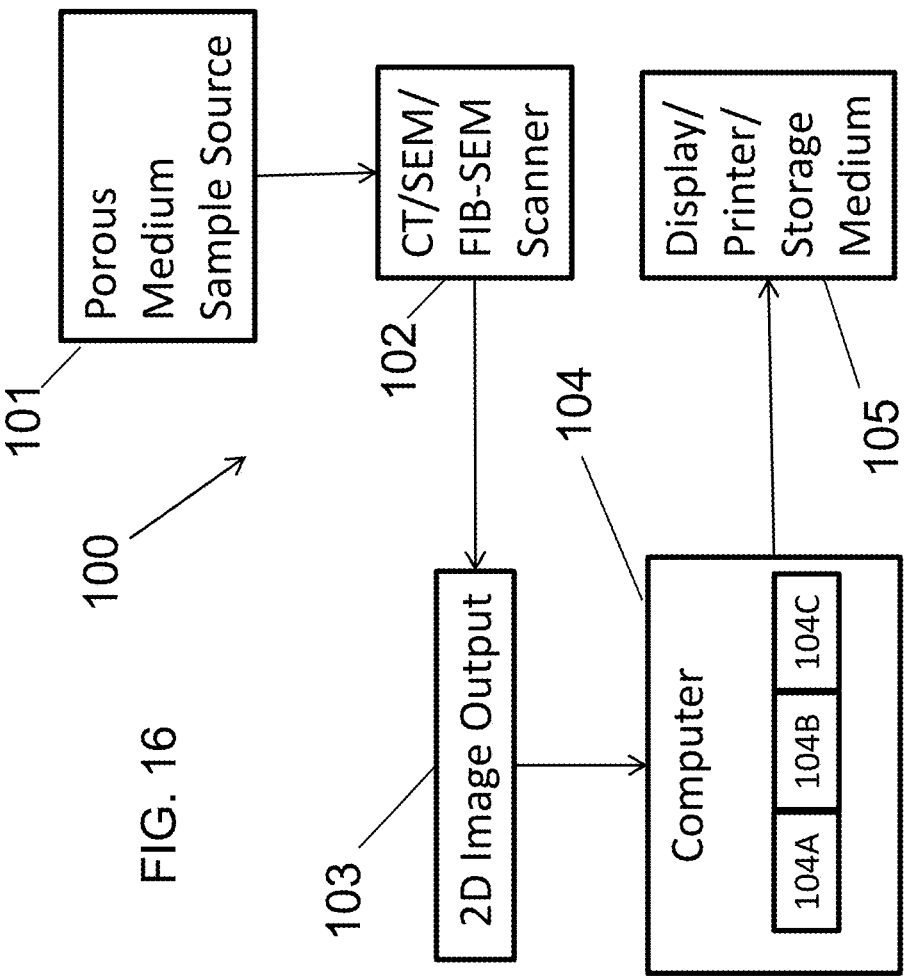

FIGS. 14A-14C schematically illustrate pore space in various degrees of increasing mineral dilation according to an example of the present application;

FIG. 15 is a graph of permeability against porosity illustrating a fit of a variation of Kozeny-Carman applying percolation porosity to the Fontainebleau sandstone dataset according to an example of the present application; and FIG. 16 is a system according to an example of the present application.

DETAILED DESCRIPTION

The present invention relates in part to methods and systems for estimating a target rock property values for rocks, such as absolute permeability, relative permeability, formation factor, elasticity, or capillary pressure values, and other porous media using unique digital rock physics techniques applied to 2D images. These methods and systems of the present invention can be suitable for application to small scale samples, such as cuttings returned to the surface in normal drilling operations and applications, where requirements for speed and volume may not be optimally met by 3D digital image volume analysis.

Absolute permeability, for example, is a transport property directly related to fluid flow through porous rock and digital rock physics offers a quality alternative for acquiring absolute permeability values without the expensive, time-consuming laboratory tests requiring an intact core or other suitably sized well shaped sample. However, having a 3D image of rock has heretofore been considered essential to computing rock properties such as permeability with digital rock physics.

FIG. 1A illustrates such a 3D segmented volume 10 segmented to pore space 12 and one or more mineral matrix phases 14. Pore space connectivity is evident in volume 10 of FIG. 1A and absolute permeability will not be zero. The requirement for a 3D volume is evident, for example, in comparing the flow paths revealed in the 3D volume providing interconnectivity to pore space 12 that do not necessarily emerge in the 2D slices of this image, see e.g., horizontal slices 16B and 16C in FIGS. 1B and 1C, respectively.

Still, estimating absolute permeability, or other target rock properties such as relative permeability, formation factor, elasticity, or capillary pressure, from 2D images remains desirable as obtaining such images is much cheaper, faster, and massive than obtaining a 3D volume, especially using FIB-SEM imaging. The importance of such 2D-based estimates becomes especially crucial when working with drill cuttings where extensive 3D imaging is economically not plausible (if not at all impossible due to the absence of appropriate sized rock material). By contrast, drill cuttings are ubiquitous to drilling for hydrocarbon development. As used herein, "drilling for hydrocarbon reservoir development" encompasses drilling for a full range of exploration and production wells and further includes drilling for facilitating recovery, e.g., for steam flooding, $CO_2$ injection, etc.

Figure 1D:
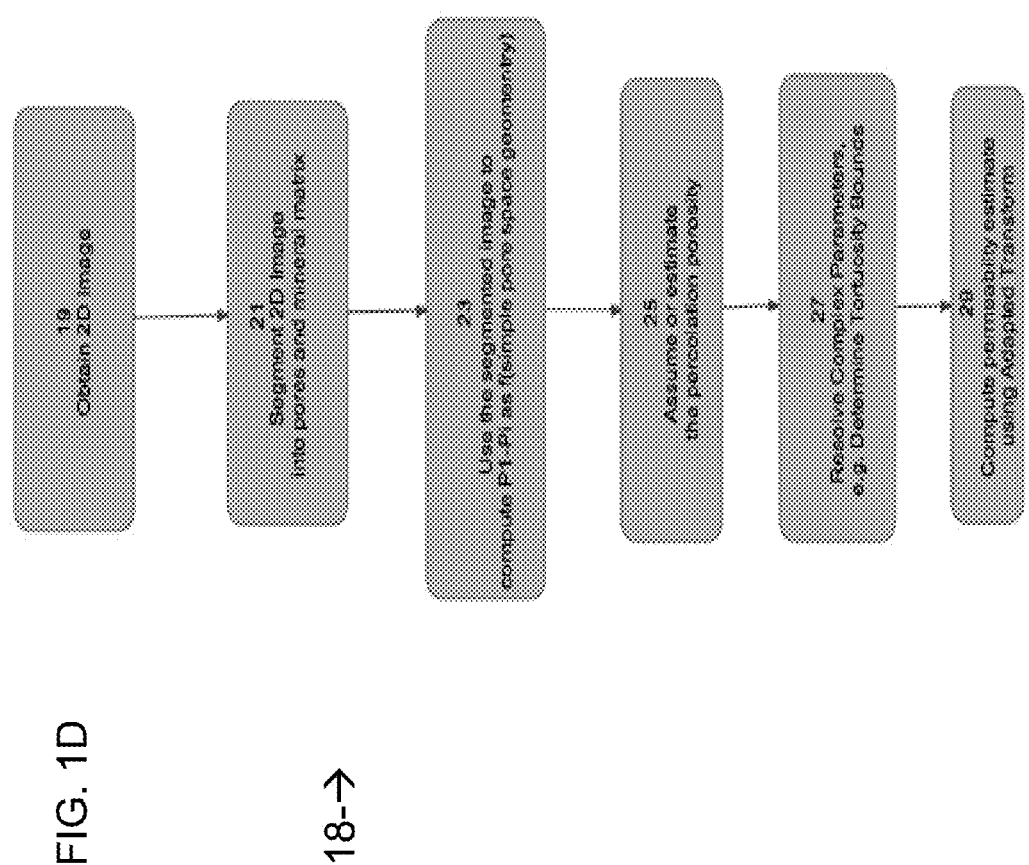
FIG. 1D is a flow diagram illustrating a work flow in accordance with an example of the present application.

Flow diagram 18 in FIG. 1D illustrates a workflow to address this need in accordance with some illustrative embodiments of the present invention. Through practices adapted from 3D volume imaging, a sample is prepared, a 2D digital image is obtained (step 19) and the digital image is segmented to pore space and mineral matrix (step 21). Further, the 2D digital image can be smoothed and/or filtered as needed to remove possible imaging artifacts that affect the rugosity of the pore walls apparent in the image.

The resulting 2D segmented image is suitable for rather accurately estimating a plurality of rock or other porous media properties as simple functions of pore space geometry. For instance, depending upon the needs of the transform, such rock or other porous media properties, such as porosity, specific surface area, and grain size diameter, can be directly computed. See step 23 (properties P1-Pi). Further, as discussed further below, some forms of useful transforms for calculating absolute permeability, for example, require that a value for percolation porosity be assumed or estimated. This is set out in optional step 25.

Illustrative embodiments discussed in greater detail below employ forms of the Kozeny-Carman transform or apply other transforms relating more complex properties like tortuosity to functions of simple pore space geometry. See step 27. Application of other transforms, e.g., Timur's equation, could relate other complex properties such as irreducible water saturation $S_{wi}$ to a function of simple pore space geometry such as porosity, specific surface area, or grain diameter.

Step 29 then calls for computing estimates of absolute permeability using a transform adapted to 2D application.

Figure 1E:
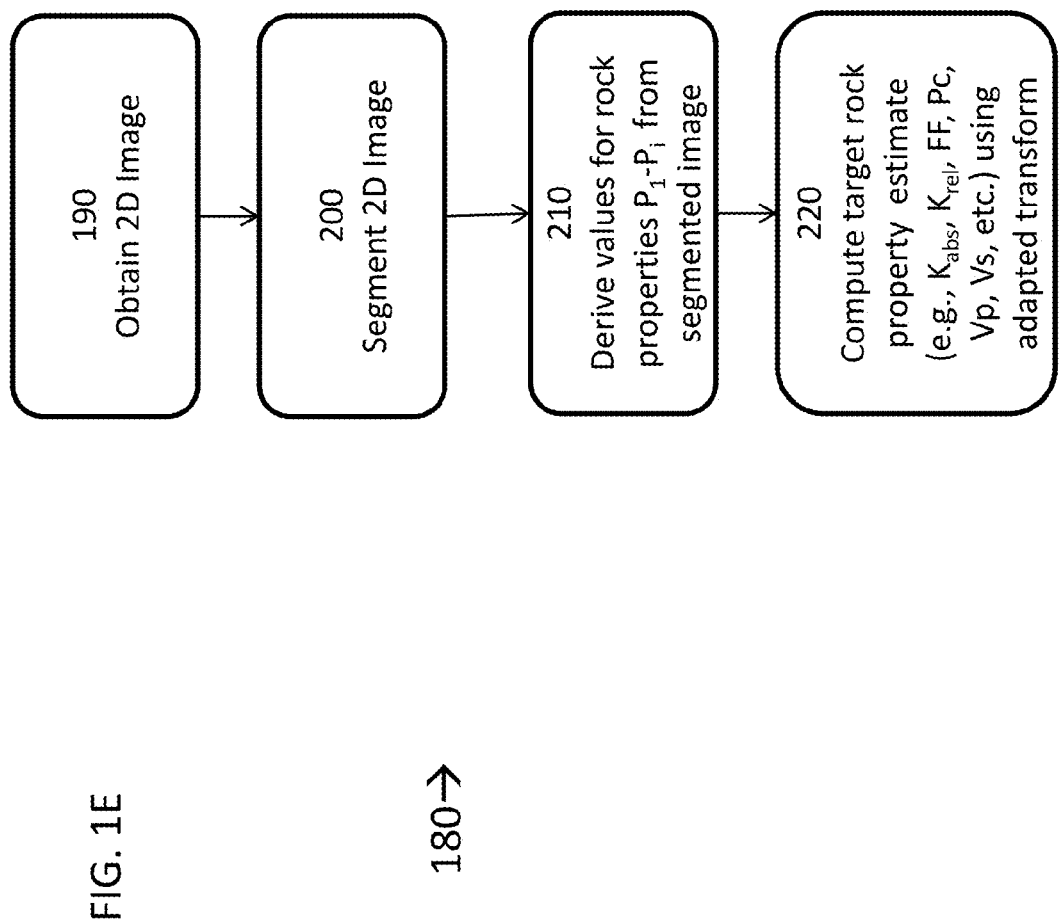
FIG. 1E is a flow diagram illustrating a work flow in accordance with an example of the present application.

Although illustrations of the method are included herein that are used for estimating absolute permeability as a target rock property, it will be understood that a method of the present invention can be used in estimating other target rock properties, such as relative permeability, formation factor, elasticity, capillary pressure, or other target rock properties. This is shown, for example, in FIG. 1E. Flow diagram 180 in FIG. 1E illustrates a workflow in this respect in accordance with some illustrative embodiments of the present invention. As indicated, through practices adapted from 3D volume imaging, a sample is prepared, a 2D digital image is obtained (step 190) and the digital image is segmented, such as to pore space and mineral matrix (step 200). Further, as indicated, the 2D digital image can be smoothed and/or filtered as needed to remove possible imaging artifacts that affect the rugosity of the pore walls apparent in the image. As indicated, the resulting 2D segmented image is suitable for rather accurately estimating a plurality of rock or other porous media properties as simple functions of pore space geometry, such as indicated in step 210 (properties P1-Pi). A target rock property estimate, such as for absolute permeability, relative permeability, formation factor, elasticity, or capillary pressure, can be computed using a transform adapted to 2D application (step 220).

As used herein, "adapted" means directly developing transforms relying on 2D adaptations of 3D properties that are functions of simple pore space geometry; solving for intermediary, more complex components such as tortuosity or irreducible water saturation as a function of simple pore space geometry and applying that value in a transform containing such complex components; or substituting expressions of simple pore space geometry for more complex component in a transform.

Figure 2A:
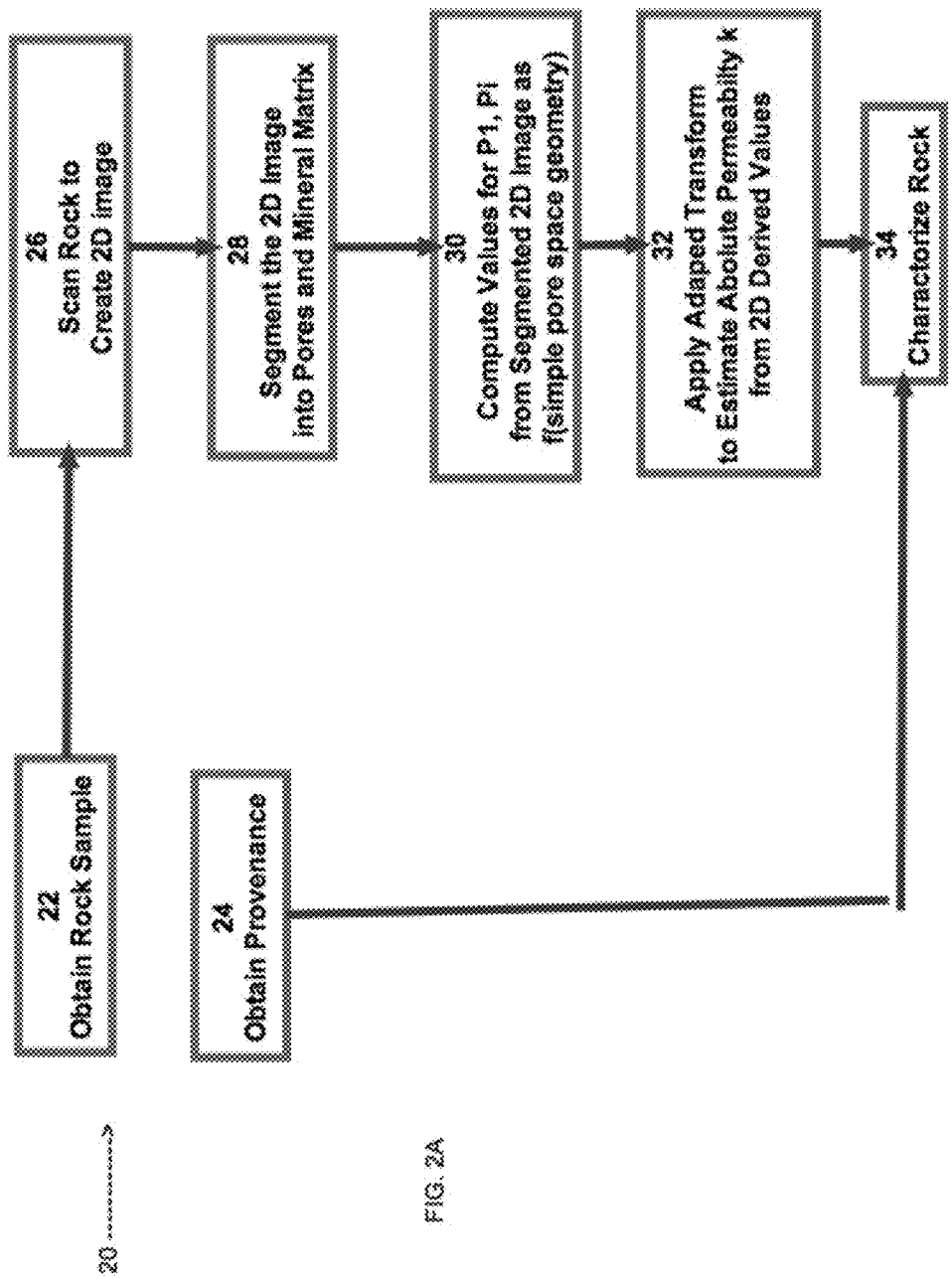
FIG. 2A is a flow diagram illustrating a work flow in accordance with an illustrative example of the present application.

Flow diagram 20 in FIG. 2A illustrates a work flow to address this need in accordance with the present invention. Step 22 addresses obtaining a rock sample and, as set out above, working in 2D allows greater flexibility in sample selection than can be practical for 3D applications. It will also be appreciated that the value of the analysis of rock structure generally requires context of where in the borehole the sample was acquired. Cores and core plugs are collected and retrieved by special operations and equipment serving to locate the collection point in the borehole by the depth of the bottom hole assembly at the time of collection. However, drill cuttings are not typically collected in place as they are fractured from the bedrock in the ordinary course of drilling. Rather such cuttings are collected from a flow of drilling mud. The mud circulates from the surface, down the drill string, and out ports or jets in the drill bit to scouring the bottom of the borehole. The fresh drill cuttings are entrained and carried with the mud returning through the annulus to the surface. Cuttings are removed from the mud through shaker tables at the surface and are available for collection. At times, appearance of rock at the shaker tables from known depositional layers can serve as "markers" to provide such context. At other times the flow of mud can be modeled to estimate the depth of the cuttings based on the time lapsed before drill cuttings appear at the surface. Such modeling can take into account, e.g., the composition, characteristics and flow rate of the mud; the dimensions, geometry, and orientation of the borehole and annulus; and the size, distribution, density and "slippage" of the drill cuttings. However acquired, this context or provenance is associated with the rock sample and is generally referenced as step 24 in FIG. 2A.

The rock sample is scanned, e.g., with a Focused Ion Beam-Scanning Electron Microscope (FIB-SEM) system, to create a 2D digital image (step 26) and at step 28 the image is segmented into pixels representing pore spaces 12 and pixels representing mineral matrix 14 (recall FIGS. 1B and 1C). Scanning and segmenting operations are directly adapted from 3D operations, but are conducted in a plurality of single 2D slices or in subsamples of a 2D single slice as set out below in greater detail. FIB-SEM systems are commercial available which can be used. The FIB component of the FIB-SEM system can act like a nanoscale scalpel to remove very thin slices of material from a sample, while the SEM captures images of the sample's structure at each slice. The methods of the present invention also can be practiced using other types of x-ray scanning equipment which can produce 2D images of a scanned sample, such as x-ray CT scanners. The FIB-SEM can be a destructive process, whereas CT scanning is non-destructive, relative to scanned portions of the sample before the final scan. Samples can be prepared for the scans, for example, in conventional ways used for the type of sample and the type of scanner being used. Samples also can be prepared for scanning, for example, by preparation methods such as those shown in U.S. Pat. No. 6,516,080 to Nur et al., which is incorporated herein in its entirety by reference.

For purposes herein, "segmentation" means a process of partitioning a digital image into multiple segments (sets of pixels). Image segmentation is typically used to locate objects and boundaries (lines, curves, etc.) in images. In segmentation of porous rock, for example, it can be used to allocate pore space and one or more non-porous phase regions and their boundaries. Image segmentation is the process of assigning a label to the pixels in an image such that pixels with the same label share certain visual characteristics. The result of image segmentation is a set of segments that collectively cover the entire image, or a set of contours extracted from the image. Each of the pixels in a region can be similar with respect to some characteristic or computed property, such as color, intensity, or texture. Adjacent regions are different with respect to the characteristic(s). General-purpose algorithms and techniques have been developed and used for image segmentation in the field of digital image processing. For example, a digital image of a rock sample can be segmented into its compositional classes. The term "compositional classes" can encompass, for example, open pores, mineral(s), optionally other types of materials, or any combinations thereof. Members of a single compositional class should possess the same composition and the same general structure relative to other compositional classes so that they influence to a similar extent the properties of the rock. As known in the field, there can be ambiguity in segmenting x-ray attenuation images (to use the X-ray microtomography example) into compositional classes of similar mineralogy because different rock minerals can have similar x-ray attenuations. Segmentation can be greatly aided if prior information about the mineral composition of the sample limits the number of possibilities for each pixel. As also known, where there is no prior information, x-ray diffraction can be used to determine mineralogy. If two compositional classes have equal or nearly equal x-ray attenuations, it may be necessary to use structural metrics to distinguish them as will be understood by those skilled in the art. These and other segmentation methods and techniques may be applied or adapted for use in a method and system of the present invention.

Returning to FIG. 2A, the 2D segmented image obtained at step 28 is used to compute a plurality of property values (step 30) necessary to solve for absolute permeability in step 32. Step 30 derives estimates in 2D as a function of simple pore space geometry for property values, most of which actually exist and are defined in 3D. For instance, porosity $\phi$ is the volume of the pore space divided by the volume of the sample. However, porosity estimates are obtained based on the area of the pore space divided by the area of the sample. Similarly, specific surface area s is approximated by the length of the boundary between pore space and mineral matrix divided by the area of the image. While the segmented images of rock samples can be complex, "simple pore space geometry", for purposes herein, covers a number of properties that can be discerned or approximated as a result of direct measurement from the segmented image. Besides porosity and specific surface area, simple pore space geometry further includes, but is not limited to, grain size and capillary diameter. The desired properties to be derived from simple pore space geometry will depend upon the specific nature of the adapted transform to be applied in step 32 which is selected or created to define a relationship between such properties and the more complicated absolute permeability. A "complex property," for purpose herein, can be a property that is related to pore space geometry but is not one of simple pore space geometry as defined herein. Complex properties can be, for example, tortuosity and irreducible water saturation, and target rock properties such as absolute permeability, relative permeability, formation factor, elasticity, and capillary pressure.

The property values derived from a 2D analysis of pore space geometry are applied in an adapted transform to compute an estimated value for absolute permeability. An adapted transform is a transform for properties traditionally not available for direct measurement or derivation from directly measurable properties available from simple pore space geometry. See step 32. This value, in the context of the provenance obtained in step 24, is then used to characterize the rock in step 34.

FIG. 2B is a flow diagram 20B of an embodiment of a workflow in accordance with FIG. 2A, applied to estimate absolute permeability k. See step 32B. Further, FIG. 2B includes set up provisions 36, here illustrated as converting property values for parameter $P_n$ of more complex properties of the selected transform into functions of pore space geometry and using the later relationship in adapting the transform to 2D application. See step 38 which might, e.g., be employed to reduce tortuosity $\tau$ into a function of the porosity estimate. In combination or alternative, values for complex parameters $P_x$ can be otherwise obtained, estimated or assumed at step 40 and used in adapting the transform of step 32B for application in deriving absolute porosity property values from 2D derived values. Once the transform of step 32B is adapted, set up 36 need not be repeated for every calculation. However, limitations of the transform of step 32B, the relationship of step 38 and/or the values used in step 40 should be understood. It is desirable that the adapted transform and its set-up be robustly applicable to a broad range of rock types. However, the present invention provides utility for frequent sampling even in more narrow ranges of application where large quantities of samples within a single rock type can nonetheless be efficiently processed without having to revisit set-up stage 36.

FIGS. 2C-2F, in combination with FIG. 2B, address other illustrative embodiments of the present invention as applied to estimating absolute permeability. FIGS. 2C-2F are limited to the steps between segmenting the 2D image (step 28) and characterizing the rock (step 34) but should be understood to include other aspects of FIG. 2B. For instance, the shaded boxes and amended reference numbers highlight adaptations and adoptions of steps 30, 32B and 36 of FIG. 2B for each of these additional illustrative embodiments. And while a range of distinct embodiments is illustrated, it should be understood that the entire host of permeability equations, empirical and theoretical, relating absolute permeability to porosity and other parameters derived from pore-space geometry can be applied within the scope of the invention in estimating permeability from 2D images.

Figure 2C:
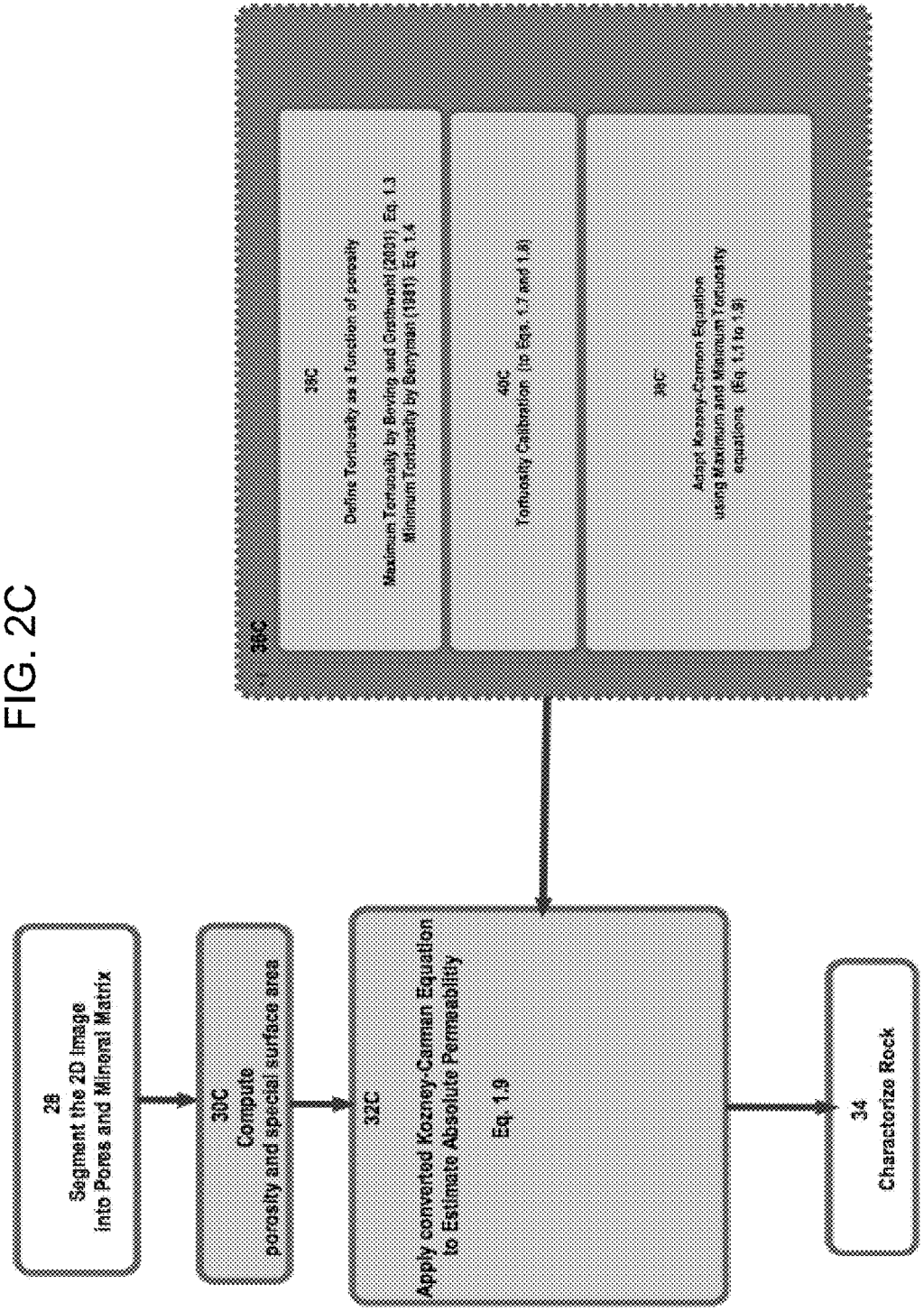
FIG. 2C is a flow diagram illustrating an excerpt of the work flow of FIG. 2B setting out with greater specificity an example of the present application directed to computing absolute permeability with a first form of a Kozeny-Carman equation.

FIG. 2C addresses the basic Kozeny-Carman equation (e.g., Mavko et al., 2009) relating the absolute (single-phase) permeability k of a 3D porous solid to its porosity $\phi$, specific surface area s, and tortuosity $\tau$ as $$k = \frac{1}{2} \frac{\phi^3}{s^2 \tau^2}, \qquad (1.1)$$

where the units of k are length squared; the units of s are one over length; and $\tau$ is non-dimensional. See Mavko, G., et al (2009). The rock physics handbook: Tools for seismic analysis of porous media, Cambridge: University Press. Naturally, the same length units have to be used fork as used for s. Specifically, if s is measured in $m^{-1}$, k is measured in $m^2$.

Recall that 1 mD=$10^{-15}$ $m^2$=$10^{-9}$ $mm^2$=$10^3$ $nm^2$. Also, 1 nD=$10^{-9}$ mD=$10^{-24}$ $mm^2$=$10^{-18}$ $mm^2$=$10^{-6}$ $nm^2$. Hence, Equation 1.1 will be $$k = \frac{10^9}{2} \frac{\phi^3}{s^2 \tau^2}, \quad (1.2)$$

if using mm$^{-1}$ for the specific surface area and mD for permeability.

Once a physical sample of rock is imaged and digitally represented (step 26), and then segmented (step 28) separating pore space from the mineral matrix, two inputs into Equation 1.2 can be computed directly from the segmented sample as a function of simple pore space geometry, here porosity $\phi$ and specific surface area s estimates. For example, after a segmentation representing pore space by zeros and mineral matrix by ones, the volume fraction of the mineral matrix in the sample is estimated as the sum of the values of pixels (in 2D) divided by the total number of pixels. The porosity $\phi$ is one minus the volume fraction of the mineral matrix. Further, the specific surface area s can be estimated as the perimeter of the pore space divided by the total area of the image. Both these calculations are addressed in the computations of step 30C for the Kozeny-Carman equation set out in the embodiment of FIG. 2C.

Figure 3A:
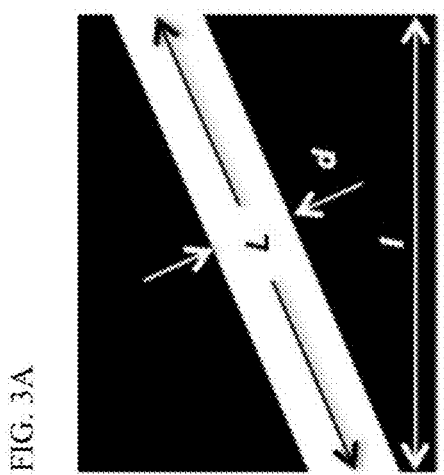
FIG. 3A is a simplified schematic representation of tortuosity.

However, while the two inputs ($\phi$ and s) are easily estimated in 2D, the tortuosity $\tau$ that is a geometric property of a 3D space is not obvious. Moreover, even if a segmented 3D image is available, it is not obvious how to define the tortuosity because the Kozeny-Carman equation is based on an idealized representation of rock as a solid block permeated by an inclined cylindrical (e.g., circular) pipe. Refer to the schematic illustration in FIG. 3A. In this highly simplified representation, the tortuosity is defined as the ratio of the length of the pipe L to the length of the block l as $\tau = L/l$. It follows from this definition that $\tau$ is always larger or equal 1 ($\tau \geq 1$). Clearly, this definition is not very useful if the pores are not perfect pipes. Nevertheless, tortuosity needs to be addressed for this and other forms of the Kozeny-Carman equation. To accomplish this task in the embodiment of FIG. 2C, set up 36C is applied using equations that relate the tortuosity to porosity in step 38C, thereby allowing conversion of the Kozeny-Carman equation to one of simple pore space geometry in step 38C'.

Several equations have been proposed for $\tau$ as a function of $\phi$. One is $$\tau = \phi^{-1.2} \quad (1.3)$$

derived from laboratory contaminant diffusion experiments by Boving and Grathwohl (2001) and another is $$\tau = (1+\phi^{-1})/2 \quad (1.4)$$

theoretically derived by Berryman (1981). See Boving, T. B., et al., 2001, Tracer diffusion coefficients in sedimentary rocks: correlation to porosity and hydraulic conductivity, Journal of Contaminant Hydrology, 53, 85-100, and Berryman, J. G., 1981, Elastic wave propagation in fluid-saturated porous media, Journal of Acoustical Society of America, 69, 416-424.

Step 40C of set up 36C calibrates these independently obtained equations based on the fundamental permeability value experimentally derived for a random dense pack of identical spheres of diameter d. This value is $$\frac{k}{d^2} = 6.8 \cdot 10^5 \frac{mD}{mm^2} = 6.8 \cdot 10^{-4} \frac{m^2}{m^2}. \quad (1.5)$$

The last value in this equation is non-dimensional and is obtained from the second value due to 1 mD=$10^{-15}$ m$^2$ and 1 mm$^2$=$10^{-6}$ m$^2$. The porosity of this pack is approximately 0.36 and the use of the pack is discussed further below.

This supports expressing the specific surface area s of such a sphere pack as a function of its porosity and grain diameter. Specifically, if the volume of rock is V and its porosity is $\phi$, the total volume of the spheres in the pack is V(1-$\phi$). Then the number N of the spheres in the pack is the ratio of this volume to the volume of an individual sphere $\pi d^3/6$ and N=6V(1-$\phi$)/$\pi d^3$.

The surface area of an individual sphere is $\pi d^2$. The surface area in the pack of spheres is N$\pi d^2$=6V(1-$\phi$)/$\pi d^3$. Hence, the specific surface area of this sphere pack is $$s = 6(1-\phi)/d. \quad (1.6)$$

By recalling Equation 1.1 and using $\phi$=0.36, we obtain k=0.001582d$^2/\tau^2$ or k/d$^2$=0.001582/$\tau^2$. However, from Equation 1.5 k/d$^2$=6.840$^4$ for the pack under examination, thereby allowing a solution for tortuosity at 1.52.

At $\phi$=0.36, Equation 1.3 gives $\tau$=3.4075 while Equation 1.4 gives $\tau$=1.8889. Calibrating these two tortuosity equations for consistency given the permeability and porosity of the random dense sphere pack, Equations 1.3 and 1.4 are reformulated then as $$\tau = 0.4476\phi^{-1.2} \quad (1.7)$$

and $$\tau = 0.4038(1+\phi^{-1}). \quad (1.8)$$

Figure 3B:
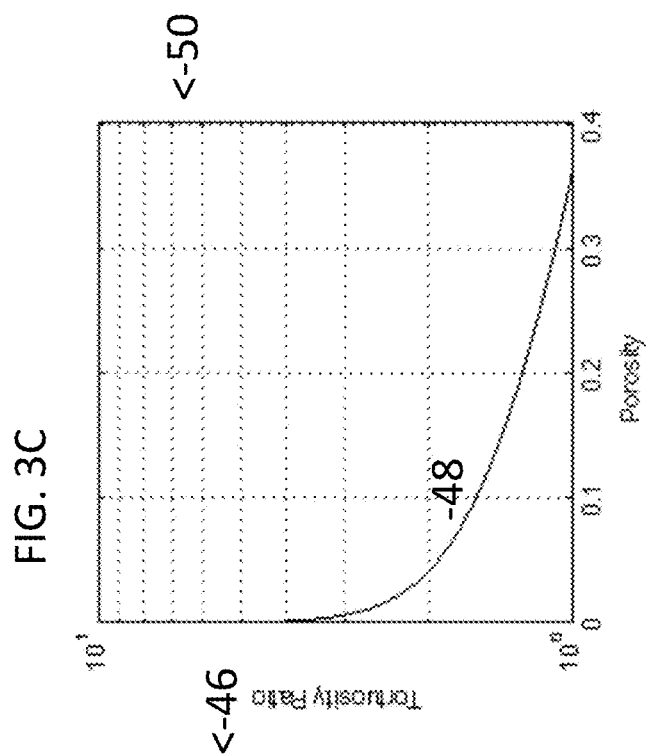
FIG. 3B is a graph of tortuosity against porosity according to an example of the present application.
Figure 3C:
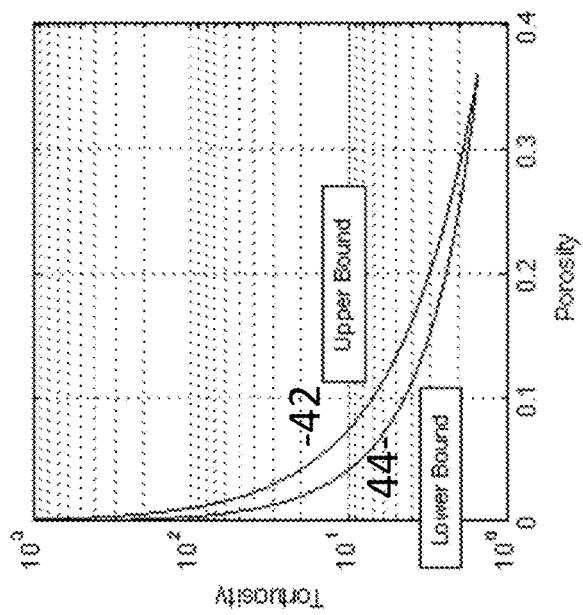
FIG. 3C is a graph of tortuosity ratio against porosity according to an example of the present application.

At $\phi$=0.36, both equations give the same tortuosity value 1.52, which is that of the sphere pack. The resulting tortuosity curves (upper bound 42 and lower bound 44) for porosity ranging from zero to 0.36 are illustrated in graph 46 in FIG. 3B. Further, the ratio of the upper to lower tortuosity bounds across this range is illustrated in curve 48 of graph 50 in FIG. 3C. The functions of defining tortuosity as a function of porosity and calibrating equations are set out as steps 38C and 40C, respectively, of set up 36C in FIG. 2C.

Figure 3D:
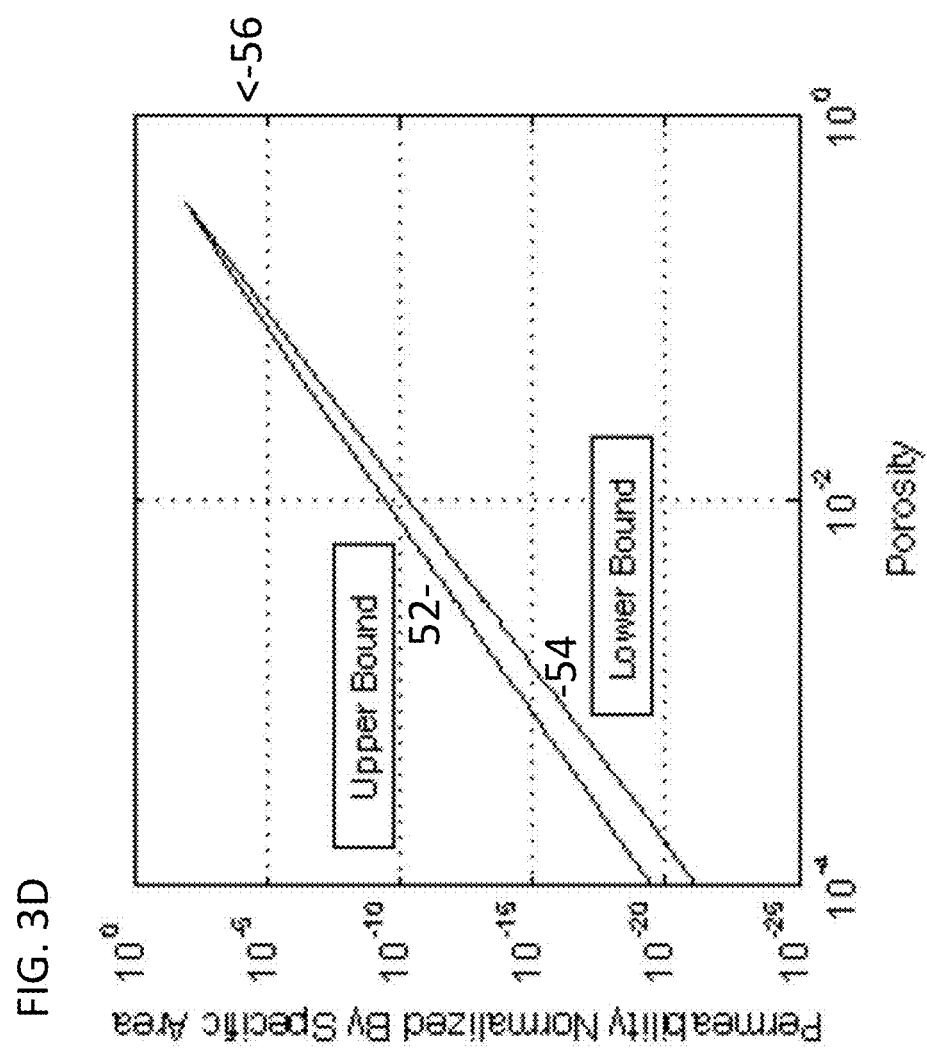
FIG. 3D is a graph of normalized permeability bounds against porosity according to an example of the present application.

The $\tau$ values from Equation 1.7 are applied as the upper tortuosity bound while those from Equation 1.8 are applied as the lower tortuosity bound. Adapting Equation 1.1 in step 38C' of set-up 36C in FIG. 2C, the upper tortuosity bound will translate into the lower permeability bound and vice versa:

$$k_- = 2.4957 \frac{\phi^{5.4}}{s^2}, \quad k_+ = 3.0665 \frac{\phi^5}{s^2(1+\phi)^2}, \quad (1.9)$$

where the "minus" subscript refers to the lower bound while the "plus" subscript refers to the upper bound. The potential accuracy of these upper and lower bounds in estimating absolute permeability k is suggested by graph 56 in FIG. 3D in which permeability, normalized by the specific surface area, is calculated for porosity between zero and 0.36 and illustrated by curves 54 for $s^2 k_-$ and 52 for $s^2 k_+$.

$$s^2 k_- = 2.4957 \phi^{5.4}, \quad s^2 k_+ = 3.0665 \frac{\phi^5}{(1+\phi)^2} \quad (1.10)$$

The work flows of flow diagrams 18 (FIG. 1D), 20 (FIG. 2A), 20B (FIG. 2B) and 20C (FIG. 2C) have been validated in the context of the embodiment of FIG. 2C. For the purposes of validation, full 3D representations and/or scans of natural and artificial rocks were created and used to compute the true absolute permeability for each representation and sample imaged using the previously validated LBM method for calculating absolute permeability. The adapted Kozeny-Carman transform was then applied to estimates for porosity and specific surface area derived for each 2D section of the 3D image. The 2D-based permeability values thus computed were compared to the 3D permeability values and/or experimental trends obtained on physical samples of similar nature.

Figure 4A:
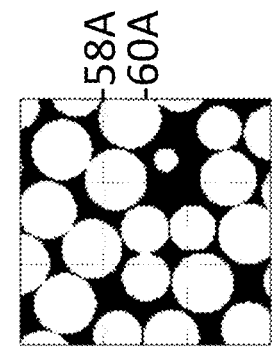
FIGS. 4A-4I are schematic illustrations of 2D slices taken normal to the vertical from 3D Finney pack models of various grain diameters according to an example of the present application.
Figure 4B:
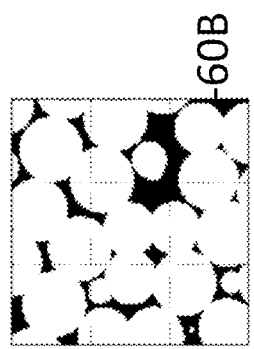
Figure 4C:
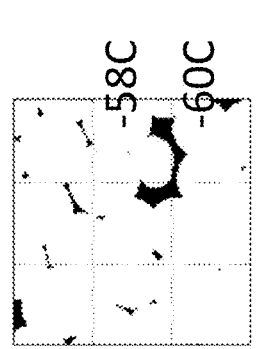

An initial validation with an idealized model is addressed in FIGS. 4A-4I and FIG. 5 for a Finney Pack. The Finney Pack is a physical pack of identical spheres in an experimentally created dense random pack. The coordinates of each sphere is available and can be used to create a digital representation of this pack in the computer by ascribing a sphere around each center. Three selected horizontal 2D slices of the virtual pack thus created are shown in FIGS. 4A-4C, 4D-4F, and 4G-4I, respectively. In this digital implementation, the diameter of each sphere 58 in FIGS. 4A-4C is 0.72 mm., however the 2D circles created at the cross section of a plane intersecting identical spheres have varying diameters. The porosity of this 3D image is 0.355. Recall the use of $\phi=0.36$ in the discussion of calibrating tortuosity (step 40C) above.

By digitally inflating each sphere 58 we can create additional packs 60B and 60C where the spheres are allowed interpenetrate creating a less idealized sample for validation. Specifically, by increasing the diameter of each sphere 58 by 10% (see FIGS. 4D-4F for selected sections of pack 60B) and then 20% (see FIGS. 4G-4I for selected sections of pack 60C), two additional packs are created with porosity 0.180 and 0.065, respectively.

Figure 4D:
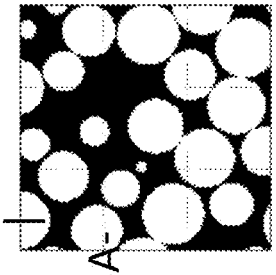
Figure 4E:
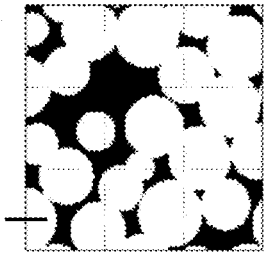
Figure 4F:
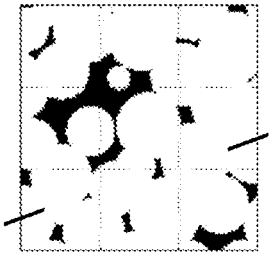
Figure 4G:
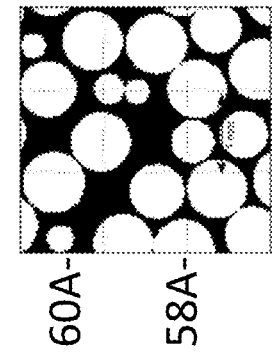
Figure 4H:
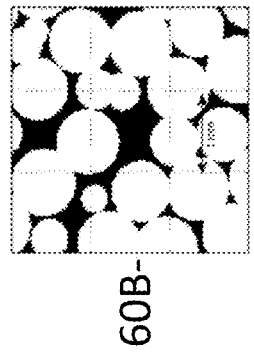
Figure 4I:
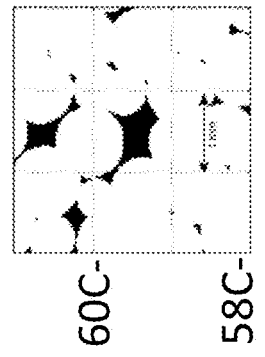
Figure 5:
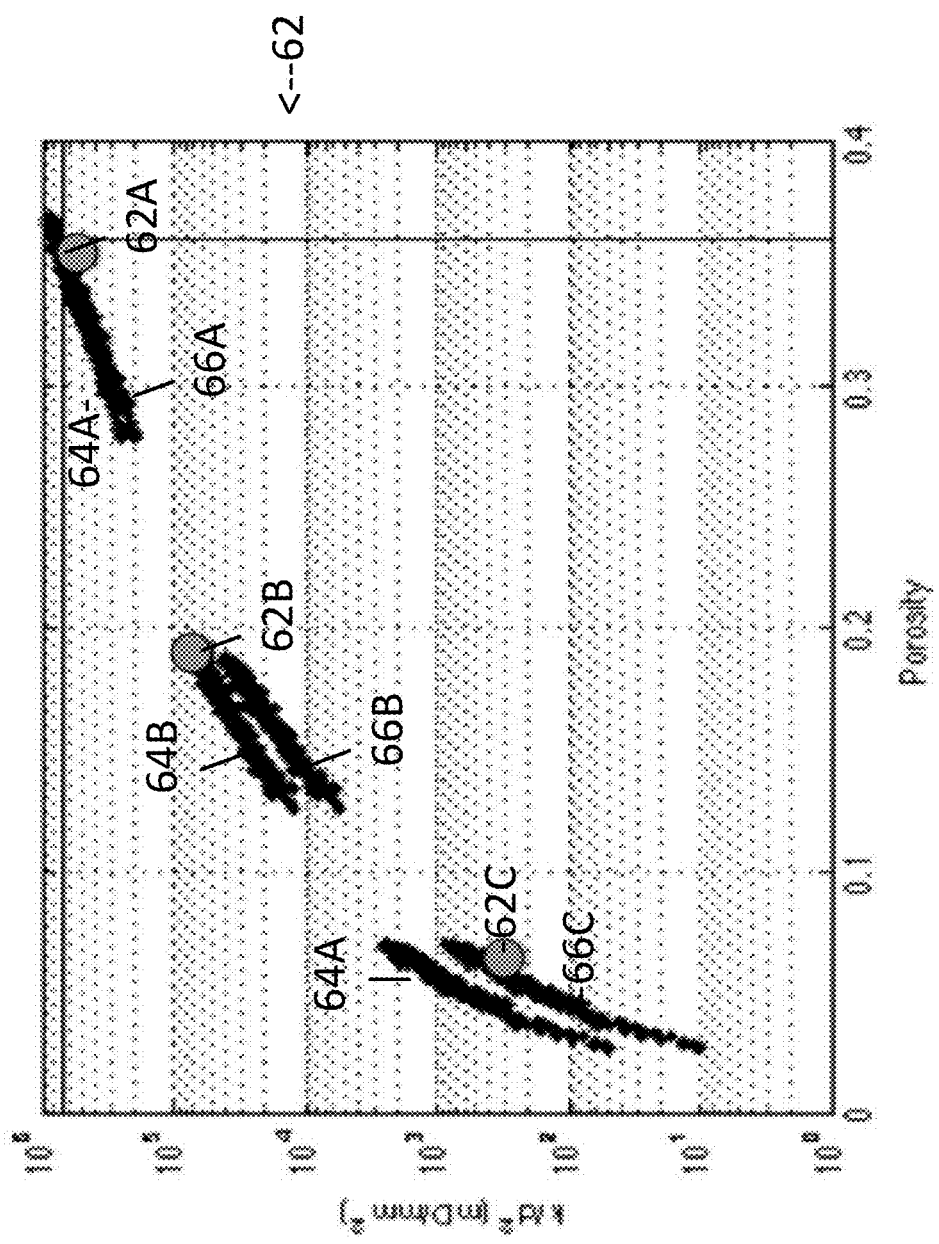
FIG. 5 is a graph of normalized permeability against porosity of the Finney pack models according to an example of the present application.
Figure 6:
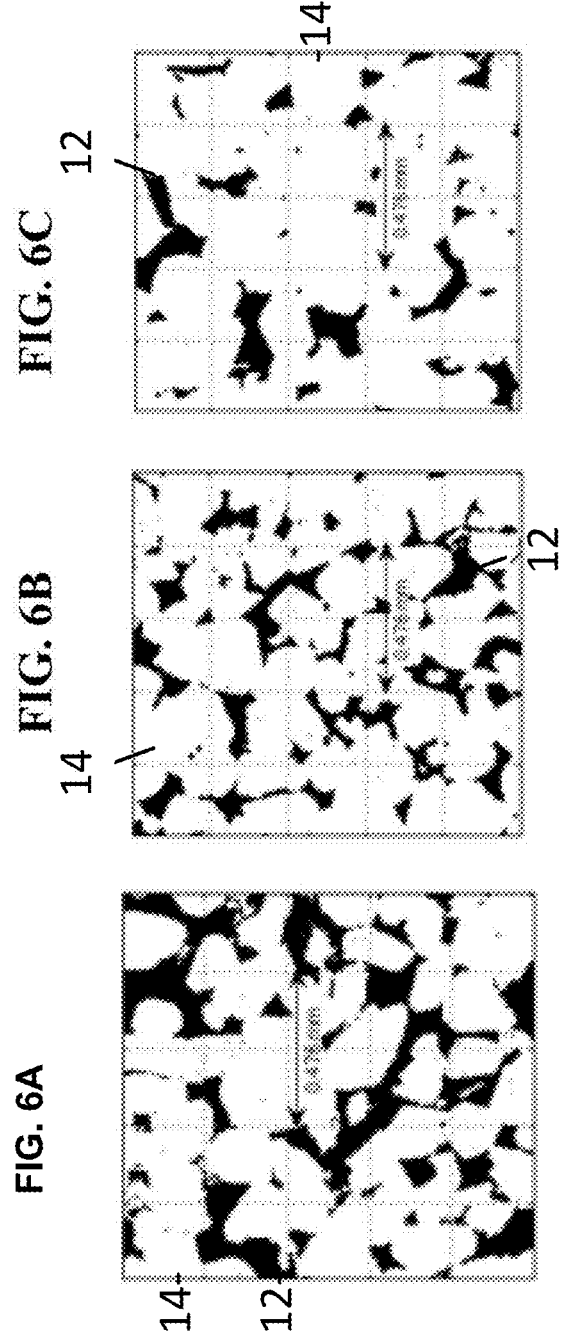
FIGS. 6A-6C are 2D segmented images created from different samples of Fontainebleau sandstone according to an example of the present application.

The computational results are shown in graph 62 of FIG. 5 for which an "A" series of data is associated with pack 60 of FIGS. 4A-4C, a "B" series of data is associated with pack 60B of FIGS. 4D-4F and a "C" series of data is associated with pack 60C of FIGS. 4g-4I. In FIG. 5, the 2D-derived permeability is calculated applying Equation 1.9 for each and every 2D section of the three 3D images (i.e., slices taken at 1 voxel increments) to produce estimates in upper (64A-C) and lower (66A-C) bounds and compared to the three 3D permeability data points (62A-C).

The nominal value of the permeability of a random dense pack with porosity 0.360 for which the ratio of the permeability to the grain size squared is 680000 $mD/mm^2$ by the lines crossing at point 62A. For the purpose of the comparison in FIG. 5, the computed 2D and 3D permeability values in mD are normalized by dividing by the square of the physical diameter of the spheres in the digitally generated dense random pack, which is $0.72 \times 0.72=0.5184$ $mm^2$.

As seen in this figure, instead of a single 2D-derived permeability-porosity pair we obtain a multitude of such pairs simply because each 2D section has porosity that can differ from that of the host 3D sample. Nevertheless, clear permeability-porosity trends (64A-C and 66A-C) are generated and validated by the tightly encompassed 3D permeability-porosity data points 62A-C.

Moving beyond idealized models, considerable validation has been undertaken on a range of rock samples, including conventional rocks, such as sandstone and carbonate, on an oil sand sample, as well as on shale samples. The 2D-derived permeability obtained using this invention has been compared to the permeability obtained on representative 3D images and the resulting 2D permeability estimates compare favorably to the 3D results. Again the LBM is used to derive absolute permeability in 3-D and will be assumed correct. Validation examples are shown in FIGS. 6 to 13.

Figure 7:
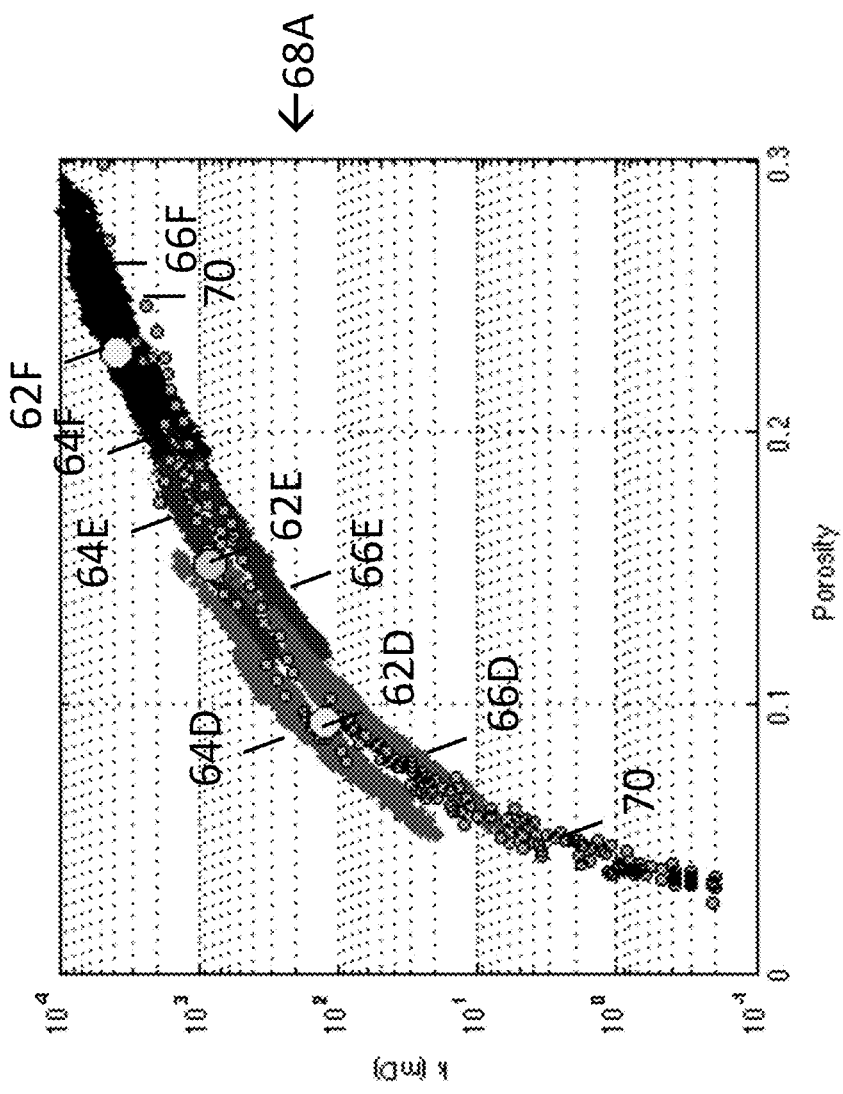
FIG. 7 is a graph of porosity $\phi$ to absolute permeability k illustrating a validation of the present invention for Fontainebleau digital samples according to an example of the present application.

FIGS. 6A-6C illustrate 2-D segmented images (recall step 28 of FIGS. 2B and 2C) representing three samples of a well explored rock, the Fontainebleau sandstone. These samples, known as H74, GW16 and A117, have very different porosity as evident from the appearance of pore space 12 to mineral matrix 14. Nevertheless, graph 68A of porosity to permeability estimates in FIG. 7 illustrates a clear trend with upper bounds 64D, 64E and 64F and lower permeability bounds 66D, 66E and 66F as computed from all 2D sections of the three Fontainebleau digital samples. Here estimate bounds 64D and 66D bracket the 3D derived value 62D for the A117 digital sample, bounds 64E and 66E bracket the 3D derived value 62E for sample GW16, and bounds 64F and 66F bracket 3D derived value 62F. The small dot symbols 70 are the results of laboratory data run physically on the Fontainebleau samples. The 2D estimates from step 32C applying the Kozeny-Carman transform as converted in step 38C' (see FIG. 2C) (Eqs. 1.9) agree very well with both the full 3D studies and the physical lab results for a set of actual rock samples.

Figure 8:
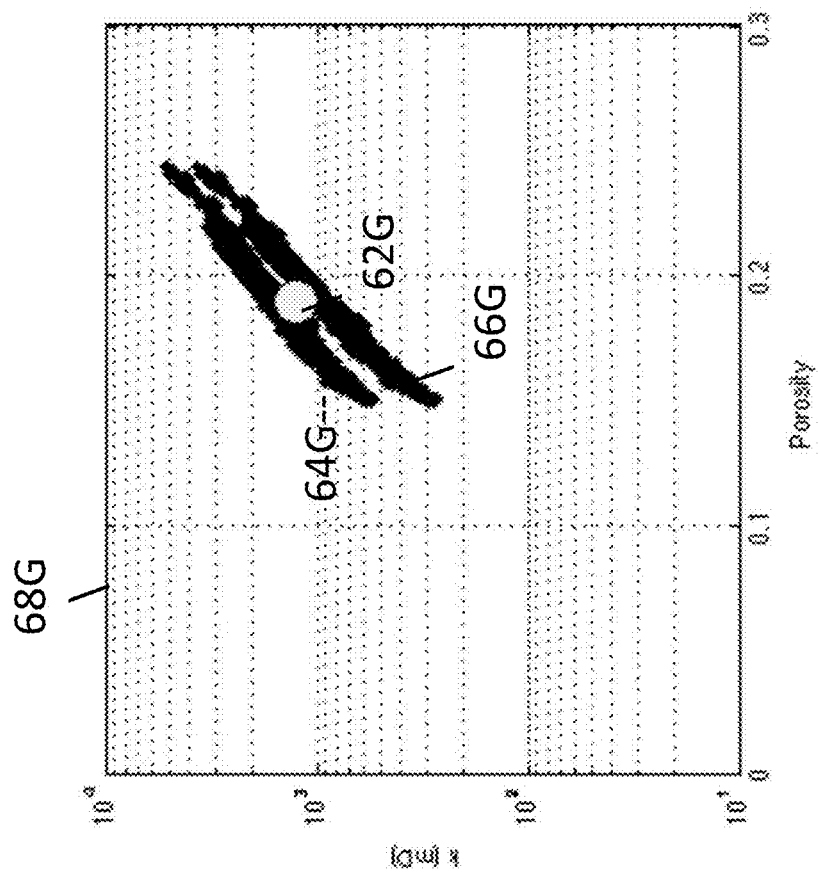
FIG. 8 is a graph of porosity $\phi$ to absolute permeability k illustrating a validation of the present invention for the Berea-200 digital sample according to an example of the present application.

FIG. 8 is the results from applying this embodiment of the present invention to another well known sample case, Berea-200 sandstone. Graph 68G illustrate upper bound 64G and lower permeability bound 66G computed from all 2D sections of the Berea-200 digital sample. The large circle 62G is for the porosity and permeability computed on a given 3D digital Berea-200 sample. Again, the 3D computation is tightly bracketed by the 2D estimates.

Figure 9:
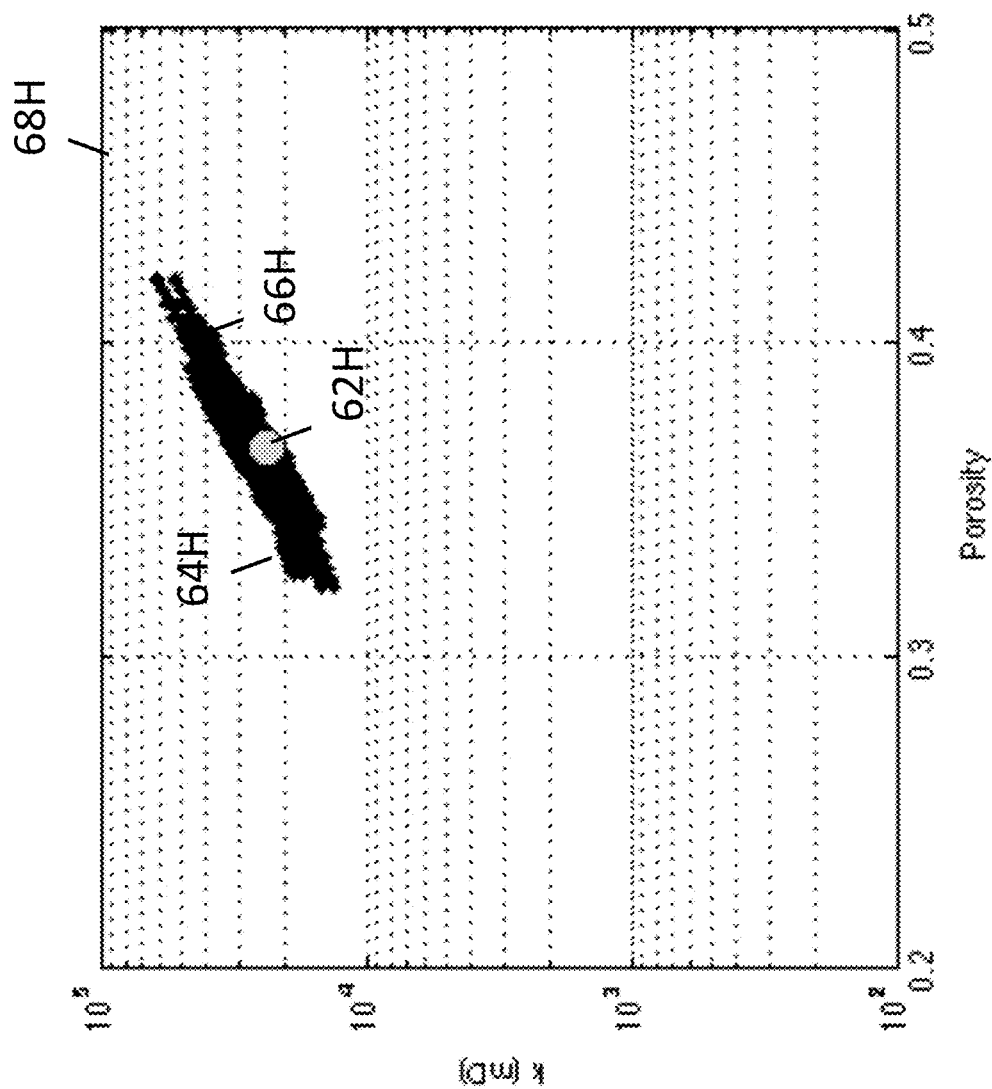
FIG. 9 is a graph of porosity $\phi$ to absolute permeability k illustrating a validation of the present invention for an oil sand digital sample according to an example of the present application.

FIG. 9 illustrates further robustness in this embodiment as applied to an oil sand sample. Here graph 68H illustrates upper and lower permeability bounds, 64H and 66H, respectively, as computed from all 2D sections of the digital sample. Again, large circle 62H plotting the porosity and permeability computed for comparison and validation from the 3D digital oil sand sample is well bracketed by the 2D derived estimates.

Figure 10:
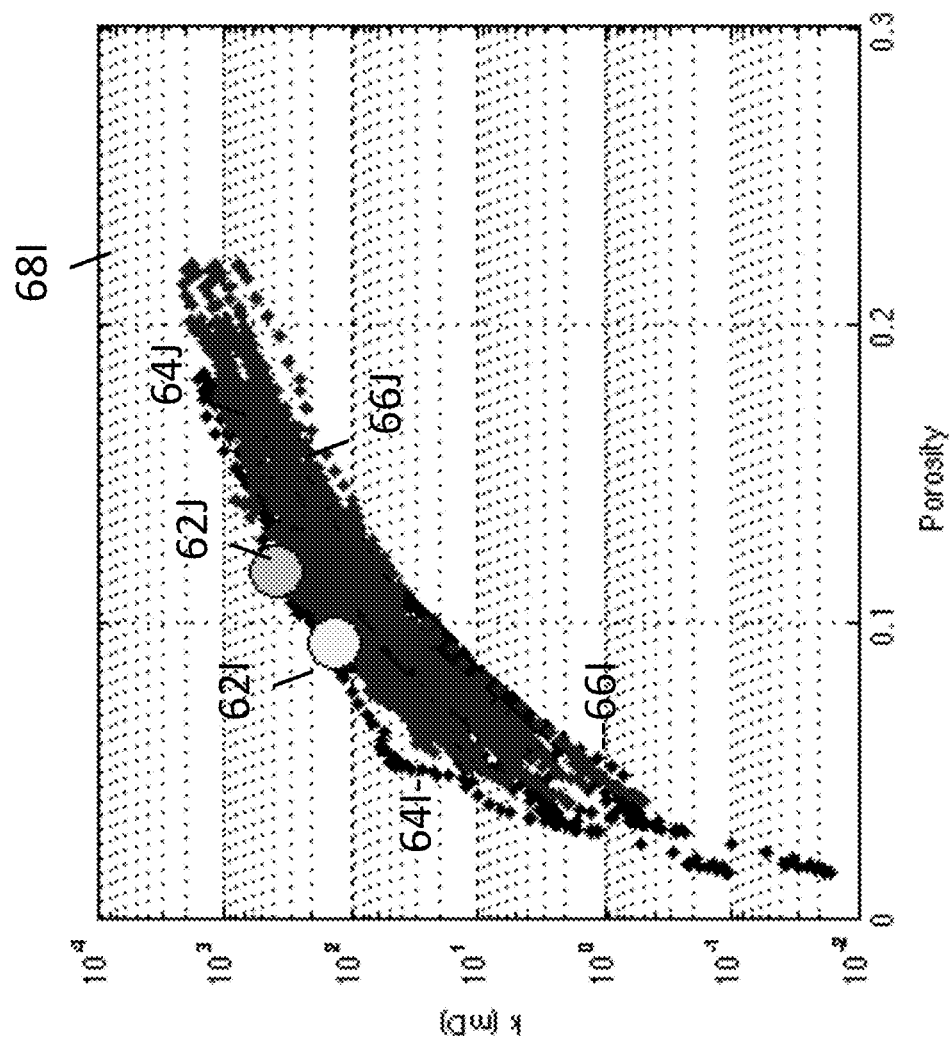
FIG. 10 is a graph of porosity $\phi$ to absolute permeability k illustrating a validation of the present invention for carbonate digital samples according to an example of the present application.

Graph 68I of FIG. 10 illustrates upper bounds 64I and 64J and lower permeability bounds, 64I and 66J, respectively, computed from all 2D sections for two different carbonate digital samples. Bounds 64H and 66H are for a carbonate sample with porosity 0.094 while bounds 64I and 66I are for the carbonate sample with porosity 0.117. The large circles 62H and 62I represent the porosity and permeability computed on the 3D digital samples for the samples with porosities of 0.094 and 0.117, respectively. In these carbonate samples, the calculated 3D porosity/permeability values was bracketed by the 2D estimates for the lower porosity and was closely tracked for the higher porosity.

Figure 11:
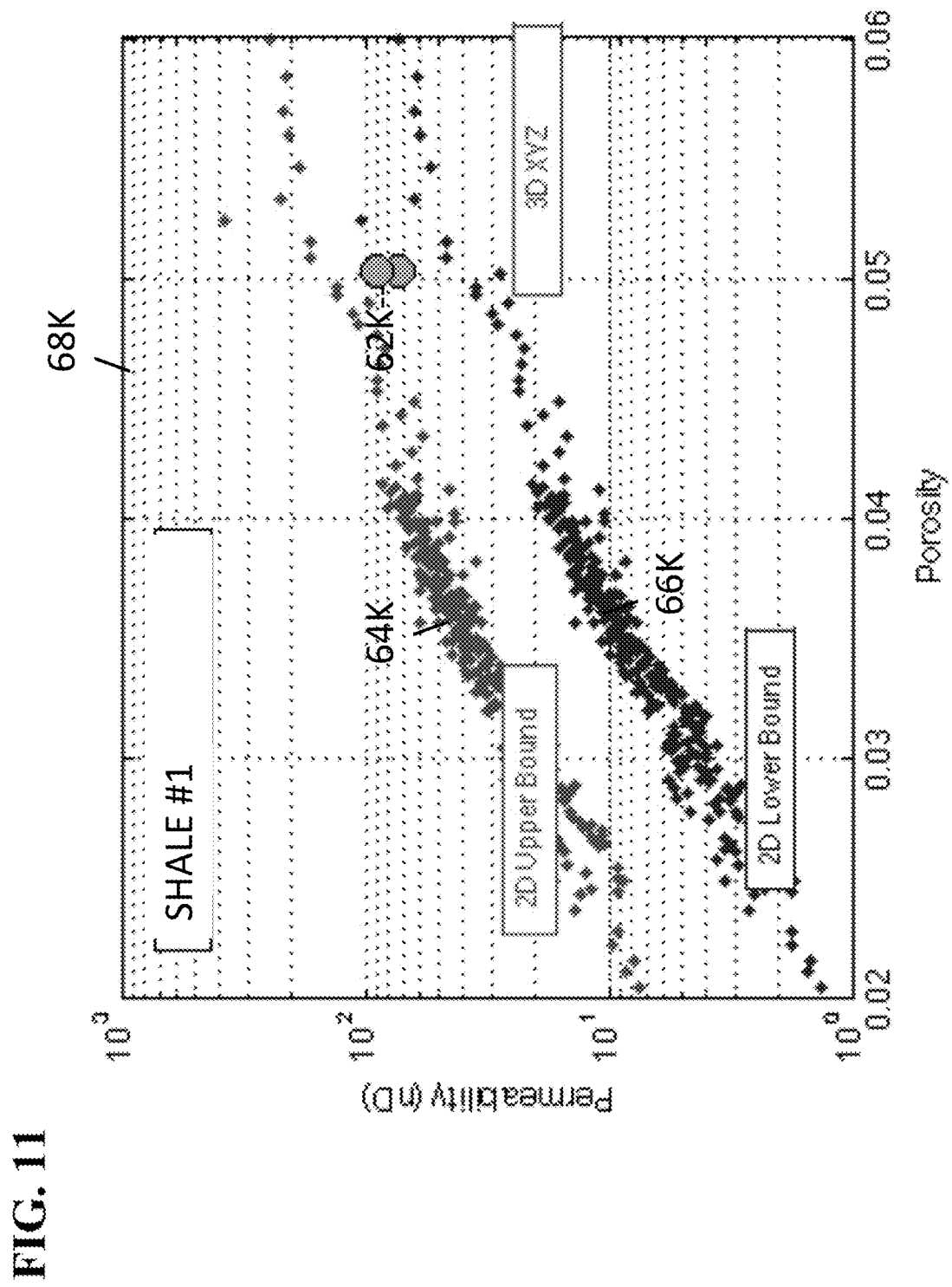
FIG. 11 is a graph of porosity $\phi$ to absolute permeability k illustrating a validation of the present invention for a shale sample against 3D results according to an example of the present application.

FIG. 11 illustrates the results of using the embodiment for estimating absolute permeability of FIGS. 2B and 2C in an application of very tight rock such as shale. Here upper bounds 64K and lower permeability bounds 66K are illustrated in Graph 68K of FIG. 11, as computed from all 2D sections of the shale sample. In graph 68K, large circles 62K are the directional permeability computed on the original 3D sample. The LBM is used as with the other 3D derivations of absolute permeability in the validations. However, in addition to filters and other usual provisions to enhance the accuracy of the digital volume, here the 3D solution also take into account under-resolved and sub-resolution pore space connectivity by adding a volume of oriented micro-cracks to the 3D volume. As a result, the porosity of the adjusted 3D sample is above the average porosity of the unadjusted 2D sections. The reason is that the 2D sections were taken as slices from the original 3D FIB-SEM image while the 3D permeability was computed from the same sample but subjected to special processing to obtain more realistic permeability values in 3D than otherwise afforded by 3D under the circumstances. Note that even though the 2D estimates in the examples of FIG. 11 have not benefited from this special processing, the upper and lower bounds demonstrate that a tight shale (or any other rock) 2D image does not have to be so specially processed in order to define the permeability trend and obtain realistic permeability estimates.

Figure 12:
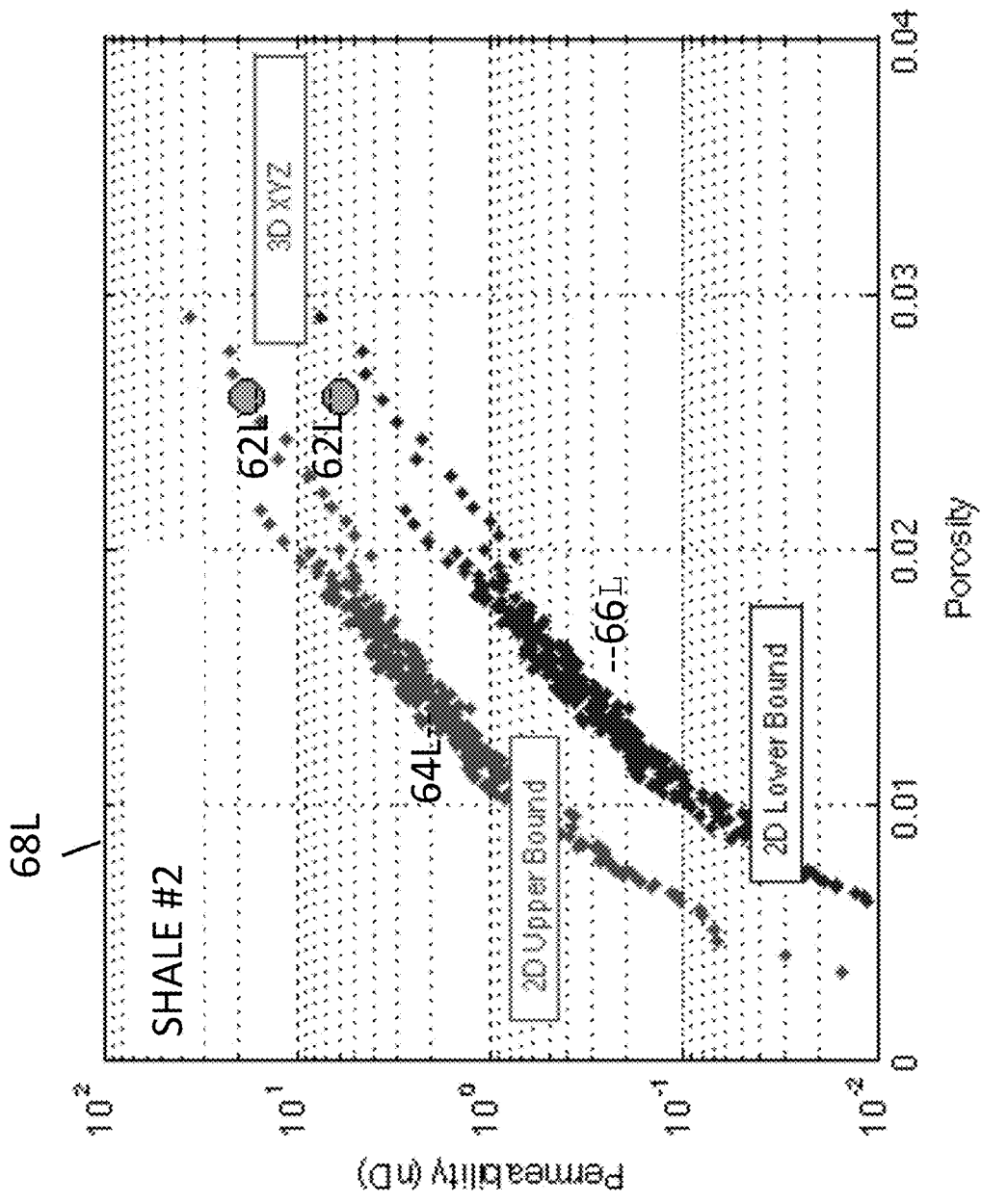
FIG. 12 is a graph of porosity $\phi$ to absolute permeability k illustrating a validation of the present invention for a different shale sample against 3D results according to an example of the present application.

FIG. 12 is the result from another shale sample. Graph 68L illustrates the directional results from 3D LBM analysis for absolute permeability with data points 62L. Here the data points are bounded by upper and lower bounds 64L and 66L, respectively. Again, while well within the trend set, data points 62L exceed the average permeability's because the 3D analysis was based on an adjusted volume while the 2D was not adjusted.

FIGS. 13A-13F illustrate a workflow implementing an embodiment of the present invention on a segmented 2D image of natural rock. The original segmented image 16D is displayed in FIG. 13A. An operator can select any part of this image for further analysis. A sample selection 74A representing substantially the whole of image 16D is illustrated in FIG. 13B. This selected 2D image is used then to compute the porosity and specific surface area as well as the tortuosity bounds. Then the Kozeny-Carman equation is used to compute the upper and lower permeability bounds that correspond to the lower and upper tortuosity bounds, respectively, as set forth above for the embodiment of FIGS. 2B/2C. These bounds represent the triangles on the ends of error bars 80 in graph 76 plotting permeability versus the porosity in FIG. 13C. The mean average 78 of these bounds is plotted as well.

This specific implementation of the present invention allows the operator to select a number of subsamples 74 from within an area inside a given image (see FIG. 13D) and to compute their porosity and permeability in the same way as for the entire image. Thus, subsample 74H of FIG. 13D is analyzed as FIG. 13E. The results for each such sample and subsample is illustrated in FIG. 13F.

Graph 76A of FIG. 13F illustrates computed absolute permeability versus porosity for each of the sub-samples imaged in FIGS. 13B and 13D. The vertical axis is the decimal logarithm of permeability in nD. The black squares 78 are the mean permeability while the vertical lines through the mean and terminating in opposing triangles are error bars 80. This can be used to create a permeability-porosity trend for the rock type under examination, all from a single sample.

Supported by this sort of validation, the embodiment of FIG. 2B, in combination with FIG. 2C, demonstrates a robust solution for a range of sandstones, carbonates and shales.

Figure 2D:
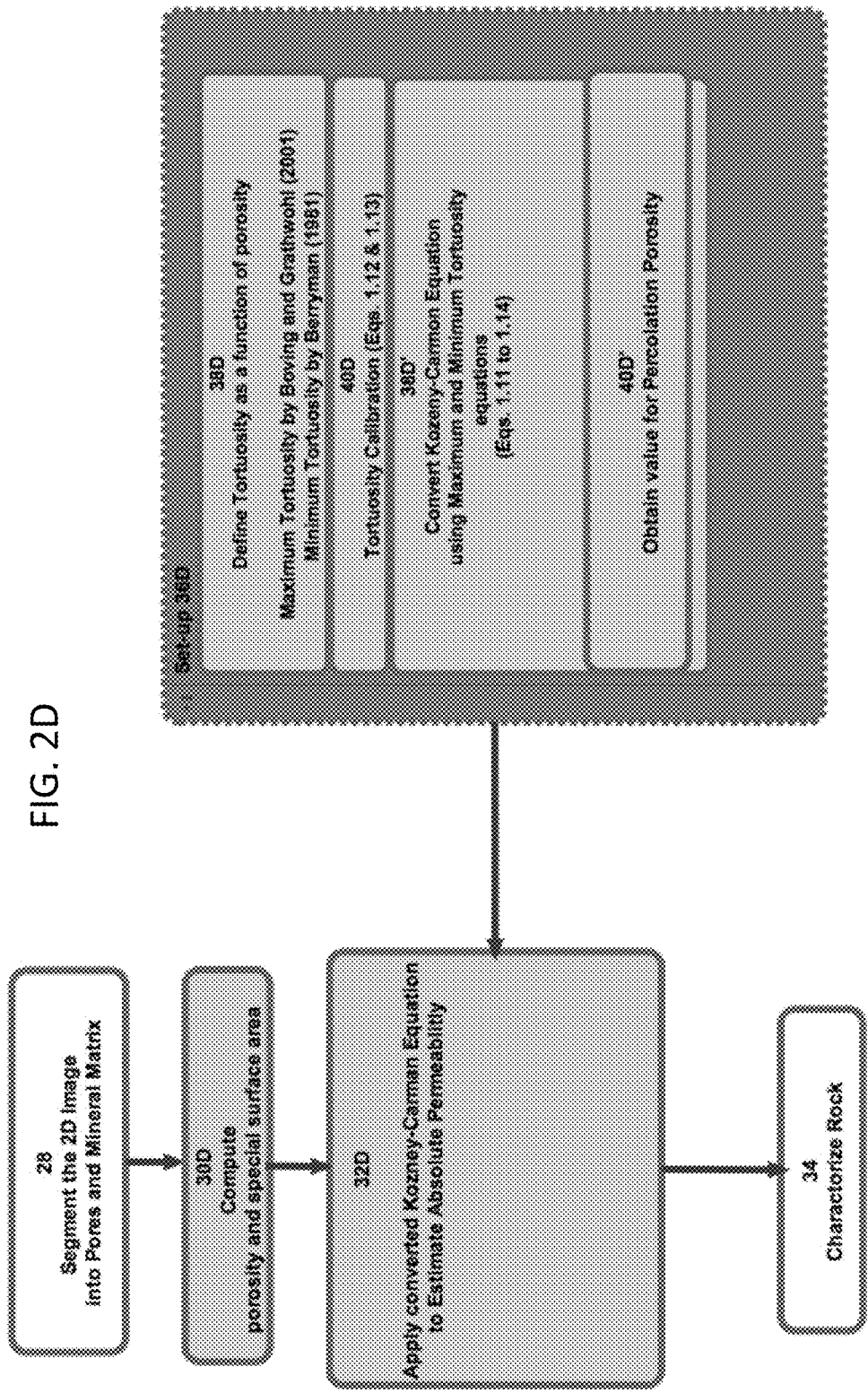
FIG. 2D is a flow diagram illustrating an excerpt of the work flow of FIG. 2B setting out with greater specificity an example of the present application directed to computing absolute permeability with a second form of a Kozeny-Carmon equation.
Figure 2E:
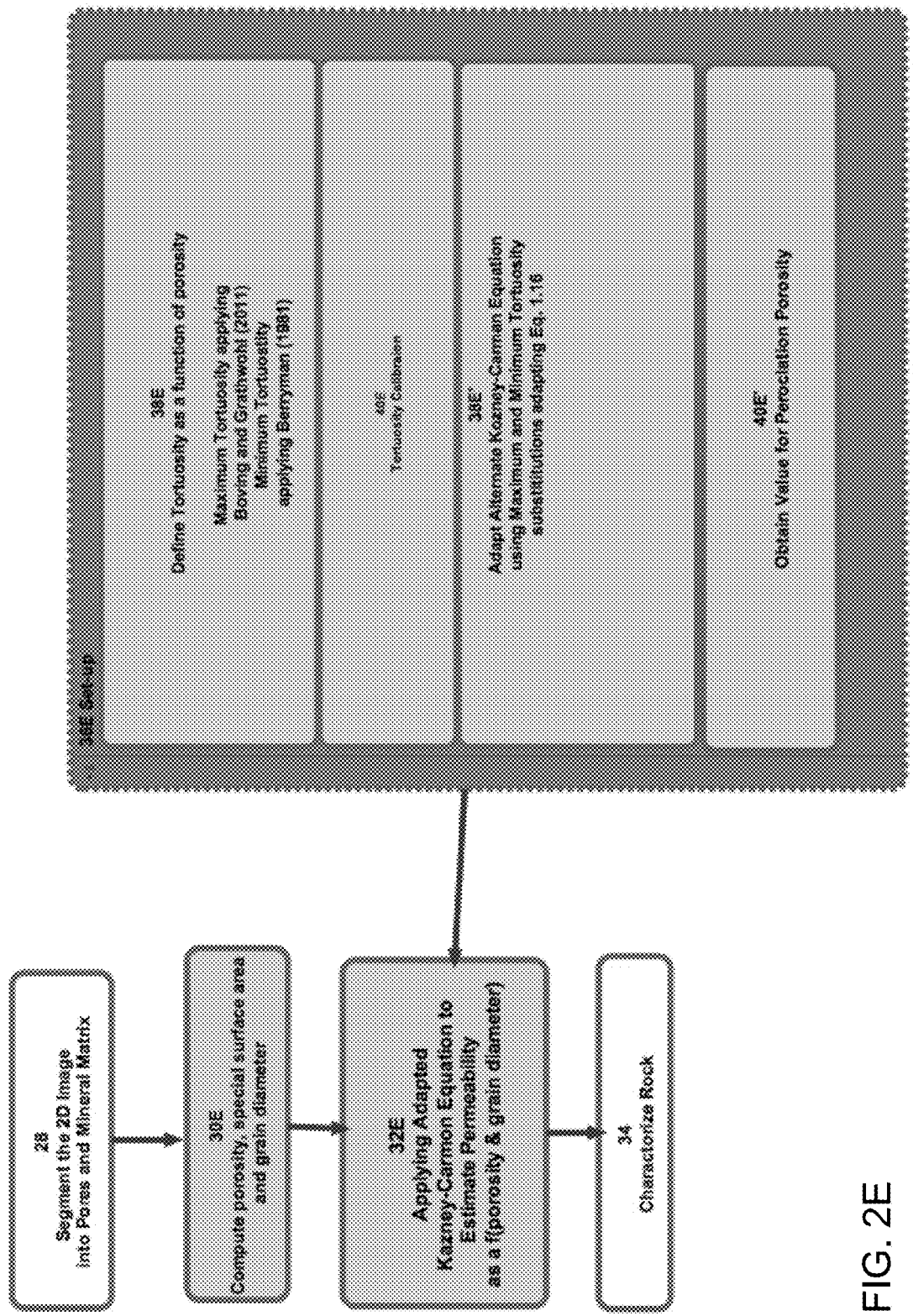
FIG. 2E is a flow diagram illustrating an excerpt of the work flow of FIG. 2B setting out with greater specificity an example of the present application directed to computing absolute permeability with a third form of a Kozeny-Carmon equation.

Returning to alternative transforms, FIG. 2D, in combination with FIG. 2B, illustrates a workflow 20D addressing a variant of the Kozeny-Carman set out in Equation 1.1. This variant includes an additional parameter, the percolation porosity $\phi_p$, which is the porosity at which the permeability of a hypothetical sample similar in its texture to the sample under examination becomes zero (Mavko et al., 1997). See Mavko, G, et al., The effect of a percolation threshold in the Kozeny-Carman relation, Geophysics 62, 1480 (1997). This can be expressed mathematically as follows:

$$k = \frac{1}{2}\frac{(\phi - \phi_p)^3}{s^2\tau^2}. \tag{1.11}$$

Set-up 36D is largely similar to set-up 36C with modifications accounting for the percolation porosity, using the same basis for converting tortuosity to a function of porosity (step 38D) and calibrating for tortuosity 40D. Thus, to include the percolation porosity $\phi_p$, modified tortuosity equations can be used in step 38D such as $$\tau = 0.4476(\phi - \phi_p)^{-1.2} \tag{1.12}$$

instead of Equation 1.7 and $$\tau = 0.4038(1+(\phi - \phi_p)^{-1}). \tag{1.13}$$

instead of Equation 1.8.

Thus Equations 1.9 and 1.10 in step 38D' are modified as $$k_- = 2.4957\frac{(\phi - \phi_p)^{5.4}}{s^2}, k_+ = 3.0665\frac{(\phi - \phi_p)^5}{s^2(1+\phi-\phi_p)^2}, \tag{1.14}$$

for Equation 1.9 and $$s^2 k_- = 2.4957(\phi - \phi_p)^{5.4}, s^2 k_+ = 3.0665\frac{(\phi - \phi_p)^5}{(1+\phi-\phi_p)^2}, \tag{1.15}$$

for Equation 1.10.

Set-up 36D adds a new step, 40D' of obtaining this third input, percolation porosity $\phi_p$. The percolation porosity is usually small, between zero and 0.03, and can typically be held constant for a group of samples of similar pore-space geometry. Values can be obtained a number of ways. For instance, percolation porosity $\phi_p$ can be computed or inferred from physical or numerical data.

Some options require that at least one 3D image representing the rock under examination or a dataset from a similar formation be available for set-up. For instance, a representative 3D segmented volume can be further processed in a dilation/erosion iteration to determine percolation porosity $\phi_p$. The mineral phase of the segmented volume can be digitally dilated and the pore space eroded in the sample until the pore space thus altered becomes disconnected and, hence, the permeability becomes zero. The porosity of this altered sample is $\phi_p$. This process of finding $\phi_p$ is illustrated schematically in FIGS. 14A-14C, showing increased dilation of mineral matrix 14 until interconnectivity of pore space 12 is interrupted in FIG. 14C. Alternatively, one can compute the disconnected pore space volume on a 3D sample and treat the porosity associated with this pore volume as the percolation porosity.

And there are other methods to analyze a physical or digital permeability-porosity dataset to infer a porosity value at which permeability becomes zero (see also Mavko et al., 1997) which can be employed for step 40D'. FIG. 15 illustrates using this form of the Kozeny-Carman equation with a percolation porosity of 0.025 to fit a curve 82 to a classical Fontainebleau sandstone dataset, see datapoints 84 (see Mavko et al., 2009). Thus, for a set of samples analogous to the Fontainebleau samples, 0.025 is a good value for percolation porosity.

Further, if these data are not available, one can simply assume $\phi_p$ and conduct calculations in the "what-if" mode to determine the bounds for the permeability thus computed depending on the percolation porosity value.

And there are other forms of the Kozeny-Carman equation. For instance, FIG. 2E, in combination with FIG. 2B, illustrates a third form of the Kozeny-Carman equation, one that uses the grain size d as well as percolation porosity:

$$k = \frac{d^2}{72} \frac{(\phi - \phi_p)^3}{[1-(\phi-\phi_p)]^2 \tau^2}, \quad (1.16)$$

The required grain size d can be computed from the specific surface area s and porosity $\phi$ from Equation 1.6 as $$d = 6(1-\phi)/s. \quad (1.17)$$

Alternatively, the average grain size or grain size distribution can be directly computed from a 2D image by using existing or new image analysis techniques. Either way, obtaining a value for d as a function of simple pore space geometry joins porosity and specific surface area in step 30E. Then these values can serve as input to Equation 1.16 as it is converted in step 38E' following tortuosity substitutions (step 38E) and calibration (step 40E) analogous to those as set out in discussions of FIGS. 2C and 2D above.

Further, other alternatives are provided by empirical transforms for permeability versus porosity and grain size or permeability versus porosity and specific surface area can be used applying the techniques described here with the porosity, specific surface area, and/or grain size directly computed from a segmented 2D image.

Figure 2F:
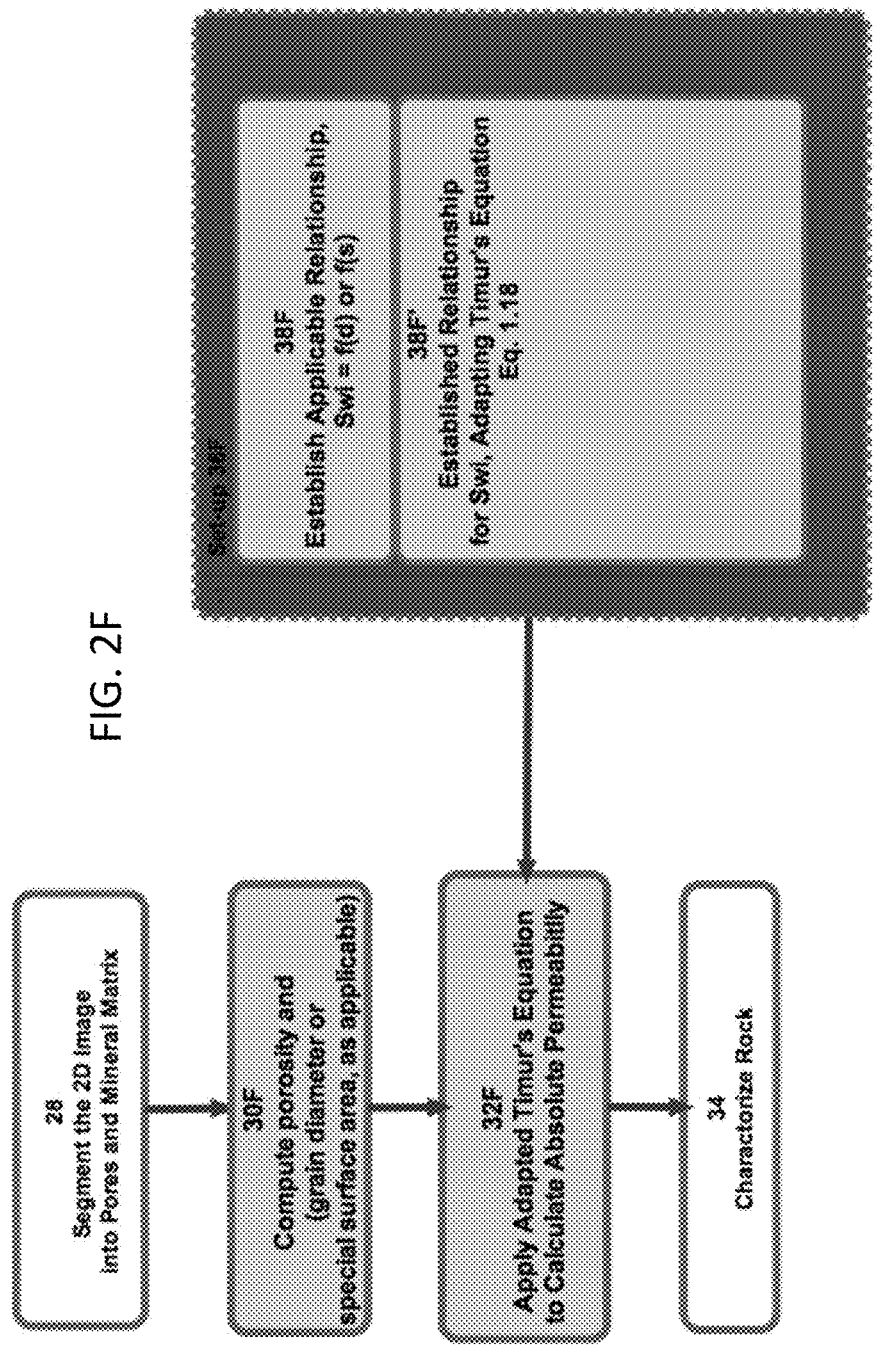
FIG. 2F is a flow diagram illustrating an excerpt of the work flow of FIG. 2B setting out with greater specificity an example of the present application directed to computing absolute permeability with a first form of Timur's transform.

In addition to variations of the Kozeny-Carman equation, there are other expressions of permeability with which the present invention can be practiced. FIG. 2F, in combination with FIG. 2B, illustrates an application of converting or otherwise adapting Timur's (1968) equation relating the permeability to porosity and irreducible water saturation $S_{wi}$:

$$k = 8581 \phi^{4.4}/S_{wi}^2, \quad (1.18)$$

where permeability is in mD and both porosity and $S_{wi}$ are in fraction of one, can be used within the workflow discussed here.

Set-up 36F proceeds based on the fact that the irreducible water saturation is determined by the capillary forces which, in turn, depend on the pore-space geometry (grain size d, capillary diameter, or specific surface area s). Using this, a relation can be established between $S_{wi}$ and d or $S_{wi}$ and s by conducting computational experiments on 3D samples or applied from any existing or newly developed empirical or theoretical relation (step 38F). Such a relationship can be used in converting Timur's equation to one of simple pore space geometry. See step 38F'. Then, once d or s is measured along with porosity on a 2D image (step 30F), absolute permeability can be computed in step 32F.

Alternatively, Equation 1.18 can be applied directly with an empirical or theoretical equation relating the irreducible water saturation to the pore-space geometry and solving for irreducible water saturation $S_{wi}$ as another input of step 30E.

The preceding sets out an example of a robust method of estimating absolute permeability k from 2D images, including methodology and illustrative examples of applications with multiple forms of Kozeny-Carman equations and integration with various empirical and theoretical relationships. Further, as indicated, the methods of the present invention can be applied to estimating other target rock properties, such as relative permeability ($k_{rel}$), capillary pressure ($P_c$), formation factor (FF), elasticity, compressional-wave or P-wave velocity (Vp), shear-wave velocity (Vs), Lamé's parameters, Young's modulus, bulk modulus, shear modulus, elastic modulus (E), electrical resistivity, hydraulic conductivity (K), specific gravity (G), Poisson's ratio (Vp/Vs), and/or other target rock properties. For example, formation factor (FF) can be estimated with a method of the present invention. As explained in U.S. Patent Application Publication No. 2011/0295580 A1, for example, Formation Factor (FF) is a rock property that has been used to determine water saturation from resistivity log measurements, and in order to make those calculations using logging techniques, a resistivity measurement is obtained from the log in a region that is thought to contain 100% water and compared to other locations in the rock that appear to contain some amount of hydrocarbon in addition to connate water.

Elastic properties from 2D images can be estimated with a method of the present invention. The elastic moduli of rock, the bulk modulus K and shear modulus G can be estimated from a 2D segmented rock image by applying one or more effective medium models to the sample under examination. One example is the differential effective medium theory (DEM) that predicts the elastic moduli of a porous medium with inclusions that can be, e.g., elliptical. One required input is the aspect ratio $\alpha$ of the inclusion which is, by definition, the ratio of the short to the long axis of the elliptical inclusion. The other required input is the porosity $\phi$ associated with these inclusions.

Based on 2D segmented image, the porosity $\phi$ can be computed and also the specific surface area S. These parameters can be then translated into the aspect ratio of an equivalent elliptical inclusion by a simple geometric transformation: at fixed porosity, the larger S the larger the eccentricity of the ellipse (a circle will have the minimum S while a greater S will require to replace this circle by an ellipsis with smaller and smaller aspect ratio $\alpha$, leading eventually to the ellipse becoming a thin crack).

Other effective medium models can be used as well as idealized shapes other than the ellipsis can be used in a similar fashion for estimating the elastic moduli from a 2D image of rock.

Once the elastic moduli K and G are computed, they can be translated into the elastic-wave velocities $V_p$ and $V_s$ as follows:

$$V_p = \sqrt{(K+4G/3)/\rho_b}, \quad V_s = \sqrt{G/\rho_b},$$

where $\rho_b$ is the bulk density of rock. It can also be evaluated from the 2D image where the mineral composition of the mineral is determined by using the CT values or any other mineralogical discriminator. The same mineralogy-based input can be used for determining the effective bulk and shear modulus of the mineral phase which are also among the inputs required to estimate the effective elastic properties from a 2D image.

Electrical properties from 2D images can be estimated with a method of the present invention. The electrical resistivity can be estimated from a 2D image by computing its porosity and then using an appropriate resistivity equation that relates the effective resistivity to that of the brine inside the pores as well as the porosity. One example is Archie's (1942) equation (Archie, G. E. "The Electrical Resistivity Log as an Aid in Determining Some Reservoir Characteristics," *Trans. AIME* 146 (1942) 54-62). Archie's (1942) equation relates the effective resistivity of rock $R_t$ to that of the water inside the pores $R_w$ as $$\frac{R_t}{R_w} = \frac{a}{\phi^m S_w^n},$$

where $\phi$ is the porosity; $S_w$ is water saturation; a is the tortuosity factor; m is the cementation exponent; and n is the saturation exponent. Both $\phi$ and $S_w$ can be determined from a 2D image and the remaining constants can be adopted from relevant experimental results, both computational and physical.

The three-dimensional porous medium which can be evaluated using a method of the present invention is not necessarily limited. The porous medium can be, for example, rock, glass, bone, soils, ceramic, sintered granular material, porous composite material, or other porous media.

The present invention further relates to a system for implementing one or more of the methods as described above. Referring to FIG. 16, a system 100 is shown which can be adapted for performing the present methods. As shown in this example, two dimensional (2D) images of the porous medium samples obtained from source 101 are generated by the scanner 102. The 2D image output 103 of the scanner can be transferred to a computer 104 having program instructions for carrying out the 2D image analysis, and the indicated data and computational analysis, to generate output/results which can be transmitted to one or more devices 105, such as a display, a printer, data storage medium, or combinations of these. The computer programs used for 2D image analysis and computations can be stored, as a program product, on at least one computer usable storage medium 104B (e.g. a hard disk, a flash memory device, a compact disc, a magnetic tape/disk, or other media) associated with at least one processor 104A (e.g., a CPU) which is adapted to run the programs, or may be stored on an external computer usable storage medium (not shown) which is accessible to the computer processor. Computer 104 can include at least one internal memory unit 104C for storage of the programs, input data and output data, and other program results, or combinations of these. The computer can output/results which can be transmitted to one or more devices 105, such as a display, a printer, external data storage medium, or any combinations of these. For output transmitted to a display, the display device 105 can be, for example, a display monitor, CRT, or other visual means of display. The computer 104 may include one or more system computers, which may be implemented as a single personal computer or as a network of computers. For example, the system can comprise one or more computers or computer systems for processing images and computing rock properties. For example, the system can comprise one or more computer systems which can comprise software to capture images, process images, segment images, estimate rock properties, and any combinations thereof. However, those skilled in the art will appreciate that implementations of various techniques described herein may be practiced in a variety of computer system configurations, including hypertext transfer protocol (HTTP) servers, hand-held devices, multiprocessor systems, microprocessor-based or programmable consumer electronics, network PCs, minicomputers, mainframe computers, and the like. The units of system 100 including scanner 102, computer 104, and output display, printer and/or data storage device/medium 105, can be connected to each other for communications (e.g., data transfer, etc.), via any of hardwire, radio frequency communications, telecommunications, interne connection, or other communication means.

The system of the present invention can be located and used off-site or on-site with respect to where the samples are obtained. If used off-site, samples can be transported to the location where the system is located. If used on-site, the system optionally can be used in a mobile enclosure such as a trailer, van, motor coach or similar device, such that it can be transported to a well site and analyses run on-site.

The present invention also includes the following aspects/embodiments/features in any order and/or in any combination:

1. A method for estimating a target rock property of a rock sample from an application of digital rock physics in 2D, comprising:
scanning a rock sample to obtain a 2D digital image of the rock sample;
segmenting the digital image to produce a digital 2D segmented image having pixels characterized as pore space and pixels characterized as mineral matrix and defining a boundary at the intersection of pore space and the mineral matrix;
deriving values for rock properties $P_1$-$P_i$ from the segmented image as a function of simple pore space geometry; and
applying a transform relationship adapted for application to a 2D segmented image environment to calculate an estimated value for a target rock property as a function of simple pore space geometry derived from the 2D segmented image.

2. The method of any preceding or following embodiment/feature/aspect, wherein the target rock property is absolute permeability, relative permeability, formation factor, elasticity, bulk modulus, shear modulus, compressional velocity, shear velocity, electrical resistivity, or capillary pressure.

3. The method of any preceding or following embodiment/feature/aspect, wherein the target rock property is absolute permeability.

4. The method of any preceding or following embodiment/feature/aspect, wherein the transform relationship adapted for application to a 2D segmented image environment is adapted by deriving a transform that is wholly a function of simple pore space geometry.

5. The method of any preceding or following embodiment/feature/aspect, further comprising obtaining a value for one or more complex properties in a set-up step, the values being suitable for application for at least a class of rocks under investigation and wherein the transform relationship adapted for application to a 2D segmented image environment otherwise applies only values obtained from the 2D segmented image as a function of simple pore space geometry.

6. The method of any preceding or following embodiment/feature/aspect, wherein the target rock property is absolute permeability, wherein the transform relationship adapted for application to a 2D segmented image environment further comprises a Kozeny-Carman equation and adaptation further comprises converting the complex property of tortuosity to one or more functions of simple pore space geometry.

7. The method of any preceding or following embodiment/feature/aspect, wherein converting the complex property of tortuosity to one or more functions of simple pores space geometry further comprises:
obtaining a relationship defining an upper bound for tortuosity as a function of simple pore space geometry;
obtaining a relationship defining a lower bound for tortuosity as a function of simple pore space geometry; and
calibrating the relationships defining the upper and lower bounds for tortuosity in a set-up step.

8. The method of any preceding or following embodiment/feature/aspect, wherein:
the relationship defining an upper bound for tortuosity, after calibration, comprises:

$$\tau = 0.4476 \phi^{-1.2}$$

the relationship defining a lower bound for tortuosity, after calibration, comprises:

$$\tau = 0.4038(1 + \phi^{-1}).$$

9. The method of any preceding or following embodiment/feature/aspect, wherein the Kozeny-Carman equation applied comprises:

$$k = \frac{10^9}{2} \frac{\phi^3}{s^2 \tau^2},$$

and
wherein deriving values for rock properties $P_1$-$P_i$ from the segmented image as a function of simple pore space geometry comprises obtaining estimates of porosity and specific surface area values; and
applying the adapted transform relationship further comprises solving for upper and lower bounds for tortuosity and inserting these computed values into the Kozeny-Carman equation to define estimates for $k_+$ and $k_-$.

10. The method of any preceding or following embodiment/feature/aspect, wherein applying a transform relationship adapted for application to a 2D segmented image environment further comprises substituting relationships defining upper and lower bounds for tortuosity into the Kozeny-Carman relationship such that bounds for absolute permeability comprise:

$$k_- = 2.4957 \frac{\phi^{5.4}}{s^2}, k_+ = 3.0665 \frac{\phi^5}{s^2(1+\phi)^2}.$$

11. The method of any preceding or following embodiment/feature/aspect, wherein:
the transform relationship adapted for application to a 2D segmented image environment further comprises a Kozeny-Carman equation and adaptation further comprises converting the complex property of tortuosity to one or more functions of simple pore space geometry;
wherein deriving values for rock properties $P_1$-$P_i$ from the segmented image as a function of simple pore space geometry comprises obtaining estimates of porosity and specific surface area; and
obtaining a value for one or more complex properties in a set-up step comprises obtaining a value for percolation porosity $\phi_p$ in set-up for a group of samples, the method of obtaining comprising selecting from a group comprising one or more of: computation through application of a dilation/erosion algorithm to the 2D segmented image, computing the porosity of a region of disconnected pore space in a 3D digital volume of a sample representative of the group, otherwise analyzing a digital data set; and analyzing a related physical data set for the porosity at which absolute permeability becomes zero.

12. The method of any preceding or following embodiment/feature/aspect, wherein tortuosity is the complex property and converting the complex property of tortuosity to one or more functions of simple pores space geometry further comprises:
obtaining and calibrating a relationship defining an upper bound for tortuosity as a function of simple pore space geometry; the relationship comprising:

$$\tau = 0.4476(\phi - \phi_p)^{-1.2}$$

obtaining and calibrating a relationship defining a lower bound for tortuosity as a function of simple pore space geometry; the relationship comprising $$\tau = 0.4038(1 + (\phi - \phi_p)^{-1}).$$

13. The method of any preceding or following embodiment/feature/aspect, wherein
the deriving values for rock properties $P_1$-$P_i$ from the 2D segmented image as a function of simple pore space geometry comprises obtaining estimates of porosity and specific surface area; and
applying the adapted transform relationship further comprises solving for upper and lower bounds for tortuosity and inserting these computed values into the Kozeny-Carman equation to define estimates for $k_+$ and $k_-$.

14. The method of any preceding or following embodiment/feature/aspect, wherein applying a transform relationship adapted for application to a 2D segmented image environment further comprises substituting relationships defining upper and lower bounds for tortuosity into the Kozeny-Carman relationship such that bounds for absolute permeability comprise:

$$k_- = 2.4957 \frac{(\phi - \phi_p)^{5.4}}{s^2}, k_+ = 3.0665 \frac{(\phi - \phi_p)^5}{s^2(1+\phi-\phi_p)^2}.$$

15. The method of any preceding or following embodiment/feature/aspect, wherein the Kozeny-Carman equation applied comprises:

$$k = \frac{d^2}{72} \frac{(\phi - \phi_p)^3}{[1 - (\phi - \phi_p)]^2 \tau^2},$$

and
wherein deriving values for rock properties $P_1$-$P_i$ from the segmented image as a function of simple pore space geometry comprises obtaining estimates of porosity, specific surface area, and grain size.

16. The method of any preceding or following embodiment/feature/aspect, wherein applying the adapted transform relationship further comprises solving for upper and lower bounds for tortuosity and inserting these computed values into the Kozeny-Carman equation to define estimates for $k_+$ and $k_-$.

17. The method of any preceding or following embodiment/feature/aspect, wherein the transform relationship adapted for application to a 2D segmented image environment was adapted from an original expression having at least one complex property which is converted to a function of simple pore space geometry.

18. The method of any preceding or following embodiment/feature/aspect, wherein applying a transform relationship for application to a 2D segmented image environment further comprises using an adaptation of Timur's equation where the complex parameter of irreducible water saturation is addressed as a function of simple pore space geometry.

19. The method of any preceding or following embodiment/feature/aspect, wherein addressing irreducible water saturation comprises:
using a relationship of irreducible water saturation and properties of simple pore space geometry selected from a group comprising one or more of grain diameter, specific surface area, or capillary diameter.

20. The present invention also relates to a method for efficiently characterizing rock traversed while drilling a borehole for hydrocarbon reservoir development with an estimated value for a target rock property, comprising:
obtaining a rock sample having a provenance of collection linked to a specific region of the borehole;

scanning the rock sample to obtain a 2D digital image of the rock sample;
segmenting the digital image to produce a 2D segmented image having pixels characterized as pore space and pixels characterized as mineral matrix and defining a boundary at the intersection of pore space and mineral matrix;
applying a transform relationship adapted for direct application to a 2D segmented image environment to calculate the estimated value for a target rock property; and
using the estimated value for the target rock property directly derived from the 2D segmented image to characterize the rock at region of the borehole.

21. The method of any preceding or following embodiment/feature/aspect, wherein:
applying a transform relationship adapted for direct application to a 2D segmented image environment to calculate the estimated value for absolute permeability further comprises applying a Kozeny-Carman equation adapted to be limited to variables of simple pore space geometry for which estimates for absolute permeability are directly calculated from the 2D segmented image.

22. The method of any preceding or following embodiment/feature/aspect, wherein the target rock property is absolute permeability, relative permeability, formation factor, elasticity, or capillary pressure.

23. The method of any preceding or following embodiment/feature/aspect, wherein scanning the rock sample to obtain a 2D digital image comprises using one or more scanning systems selected from the group consisting of focused ion beam scanning electron microscope; x-ray tomography; synchrotron, microtomography, and microradiology.

24. The method of any preceding or following embodiment/feature/aspect, wherein the target rock property is absolute permeability, and applying the adapted Kozeny-Carman equation further comprises:
estimating a minimum value for absolute permeability $k_-$ based on the relationship:

$$k_-=2.4957(\phi^{5.4}/s^2)$$

where porosity $\phi$ is estimated as the number of pore space pixels divided by the total number of pixels in the 2D segmented image; and
specific surface area s is estimated as the length of the boundary at the intersection of the pore space and the solid matrix divided by the area of the 2D segmented image.

25. The method of any preceding or following embodiment/feature/aspect, wherein applying the adapted Kozeny-Carman equation further comprises:
bounding the estimated value for absolute permeability $k_-$ between the estimated minimum $k_-$ and an estimated maximum $k_+$; and
estimating the maximum value for absolute permeability $k_+$ based on the relationship:

$$k_+=3.0665[\phi^5/s^2(1+\phi)^2],\text{ and}$$

estimating a minimum value for absolute permeability $k_-$ based on the relationship:

$$k_-=2.4957(\phi^{5.4}/s^2).$$

26. The method of any preceding or following embodiment/feature/aspect, wherein using the calculated estimate value for the target rock property directly derived from the 2D segmented image to characterize the rock comprises sampling at multiple locations throughout a zone of interest to produce estimates with a continuity useful for defining the boundaries of a zone of interest in a time frame useful for the drilling program.

27. The method of any preceding or following embodiment/feature/aspect, wherein using the estimated value the target rock property directly derived from the 2D segmented image to characterize the rock comprises sampling and making estimates substantially continuously to augment LWD data to facilitate understanding a length along the borehole.

28. The method of any preceding or following embodiment/feature/aspect, wherein:
obtaining the rock sample comprises using rock samples collected from drill cuttings in the ordinary course of drilling and associating the drill cutting to an axial depth in the borehole as a function of time to appearance at the surface and
using the estimated value for the target rock property directly derived from the 2D segmented image to characterize the rock comprises sampling at multiple locations throughout a zone of interest to produce estimates with a continuity useful for defining the boundaries of a zone.

29. The method of any preceding or following embodiment/feature/aspect, wherein using the estimated value for the target rock property derived from the 2D segmented image to characterize the rock comprises sampling and making estimates nearly continuously to augment LWD data to facilitate understanding the rock across an interval in the borehole.

30. The present invention also relates to a method for efficiently characterizing rock traversed while drilling a borehole for hydrocarbon reservoir development with an estimated an estimated absolute permeability value k, comprising:
obtaining a rock sample having a provenance of collection linked to a specific region of the borehole;
scanning the rock sample to obtain a 2D digital image of the rock sample, the scanning comprising using one or more scanning systems of a group comprising: focused ion beam scanning electron microscope; x-ray tomography; synchrotron, microtomography, and microradiology;
segmenting the digital image to produce a 2D segmented image having pixels characterized as pore space and pixels characterized as solid matrix and defining a boundary at the intersection of pore space and solid matrix;
applying a Kozeny-Carman equation adapted for direct application to a 2D segmented image environment with which an estimate is directly calculated from the 2D segmented image for absolute permeability; and
using the estimate for absolute permeability calculated from the 2D segmented image to characterize the rock at the location in the borehole.

31. The method of any preceding or following embodiment/feature/aspect, wherein:
applying the Kozeny-Carman equation adapted for direct application to a 2D segmented image environment further comprises:
applying the Kozeny-Carman equation adapted from:

$$k=\tfrac{1}{2}(\phi^3/s^2\tau^2)$$

where:
$\phi$ is porosity;
s is specific surface area; and
$\tau$ is tortuosity; and
tortuosity $\tau$ is replaced with a relation that is a function of porosity $\phi$ and specific surface area s derived through means comprising one or more of a group comprising empirical transform, theoretical physics, and calibration techniques;
estimating porosity as the number of pore space pixels divided by the total number of pixels in the 2D segmented image; and
estimating specific surface area s as the length of the boundary at the intersection of pore space and solid matrix divided by the area of the 2D segmented image.

32. The method of any preceding or following embodiment/feature/aspect, wherein applying an adapted Kozeny-Carman equation further comprises:
using a first tortuosity relationship $\tau=0.4476\phi^{-1.2}$ in estimating a lower bound for absolute permeability $k_-$ according to the following relationship:

$$k_-=2.4957(\phi^{5.4}/s^2).$$

33. The method of any preceding or following embodiment/feature/aspect, wherein applying an adapted Kozeny-Carman equation further comprises estimating absolute permeability by defining lower and upper boundaries, and further comprising:
using a second tortuosity relationship $\tau=0.40381(1+\phi^{-1})/2$ in estimating an upper bound for absolute permeability $k_+$ according to the following relationship:

$$k_+=3.0665[\phi^5/s^2(1+\phi)^2].$$

34. The method of any preceding or following embodiment/feature/aspect, wherein:
applying the Kozeny-Carman equation adapted for direct application to a 2D segmented image environment further comprises:
applying the Kozeny-Carman equation adapted from:

$$k=\tfrac{1}{2}[(\phi-\phi_p)^3/s^2\tau^2]$$

where:
$\phi$ is porosity;
$\phi_p$ is percolation porosity;
s is specific surface area; and
$\tau$ is tortuosity; and
tortuosity $\tau$ is replaced with a relation that is a function of porosity $\phi$ and specific surface area s derived through means comprising one or more of a group comprising empirical transform, theoretical physics, and calibration techniques;
estimating porosity $\phi$ as the number of pore space pixels divided by the total number of pixels in the 2D segmented image; and
estimating specific surface area s as the length of the boundary at the intersection of pore space and solid matrix divided by the area of the 2D segmented image.

35. The method of any preceding or following embodiment/feature/aspect, wherein applying the adapted Kozeny-Carman equation further comprises:
using a first tortuosity relationship $\tau=0.4476(\phi-\phi_p)^{-1.2}$ in estimating a lower bound for absolute permeability $k_-$ according to the following relationship:

$$k_-=2.4957[(\phi-\phi_p)^{5.4}/s^2].$$

36. The method of any preceding or following embodiment/feature/aspect, wherein applying the adapted Kozeny-Carman equation further comprises estimating absolute permeability by defining lower and upper boundaries, and further comprising:
using a second tortuosity relationship $\tau=0.40381(1+(1+(\phi-\phi_p)^{-1})/2$ in estimating an upper bound for absolute permeability $k_+$ according to the following relationship:

$$k_+=3.0665[(\phi-\phi_p)^5/s^2(1+\phi-\phi_p)^2].$$

37. The method of any preceding or following embodiment/feature/aspect, wherein:
applying the Kozeny-Carman equation adapted for direct application to a 2D segmented image environment further comprises:
applying the Kozeny-Carman equation adapted from:

$$k=d^2(\phi-\phi_p)^3/72[1-(\phi-\phi_p)]^2\tau^2)$$

where:
$\phi$ is porosity;
$\phi_p$ is percolation porosity;
d is grain diameter;
s is specific surface area; and
$\tau$ is tortuosity; and
tortuosity $\tau$ is replaced with a relation that is a function of porosity $\phi$ and specific surface area s derived through means comprising one or more of a group comprising empirical transform, theoretical physics, and calibration techniques;
estimating porosity $\phi$ as the number of pore space pixels divided by the total number of pixels in the 2D segmented image; and
estimating specific surface area s as the length of the boundary at the intersection of pore space and solid matrix divided by the area of the 2D segmented image.

38. The present invention also relates to a method for efficiently characterizing rock traversed while drilling a borehole for hydrocarbon reservoir development with an estimated an estimated absolute permeability value k, comprising:
obtaining a rock sample having a provenance of collection linked to a specific region of the borehole;
scanning the rock sample to obtain a 2D digital image of the rock sample, the scanning comprising using one or more scanning systems of a group comprising: focused ion beam scanning electron microscope; x-ray tomography; synchrotron, microtomography, and microradiology;
segmenting the digital image to produce a 2D segmented image having pixels characterized as pore space and pixels characterized as solid matrix and defining a boundary at the intersection of pore space and solid matrix;
applying Timur's equation adapted for direct application to a 2D segmented image environment with which an estimate is directly calculated from the 2D segmented image for absolute permeability; and
using the estimate for absolute permeability calculated from the 2D segmented image to characterize the rock at the location in the borehole.

39. The method of any preceding or following embodiment/feature/aspect, wherein applying a transform relationship for application to a 2D segmented image environment using an adaptation of Timur's equation addresses the complex parameter of irreducible water saturation as a function of simple pore space geometry.

40. The method of any preceding or following embodiment/feature/aspect, wherein addressing irreducible water saturation further comprises:
using a relationship of irreducible water saturation and properties of simple pore space geometry selected from a group comprising one or more of grain diameter, specific surface area, or capillary diameter.

41. The present invention also relates to a method for efficiently estimating absolute permeability k of rock traversed while drilling a borehole for hydrocarbon reservoir development, comprising:
obtaining a plurality of rock samples, each having a provenance of collection linked to a specific region of the borehole, the obtaining further comprising using rock samples collected from drill cuttings from drilling operations and associating the drill cutting to an axial depth in the borehole;
scanning the rock sample to obtain a 2D digital image of the rock sample;
segmenting the digital image to produce a 2D segmented image having pixels characterized as pore space and pixels characterized as solid matrix and defining a boundary at the intersection of pore space and solid matrix;

estimating porosity φ as the number of pore space pixels divided by the total number of pixels in the 2D segmented image;
estimating specific surface area s as the length of the boundary at the intersection of pore space and solid matrix divided by the area of the 2D segmented image;
estimating a lower bound for absolute permeability $k_-$ according to the following relationship:

$$k_-=2.4957(\phi^{5.4}/s^2);$$

estimating an upper bound for absolute permeability $k_+$ according to the following relationship:

$$k=3.0665[\phi^5/s^2(1+\phi)^2]; \text{ and}$$

using the lower and upper abound estimates for absolute permeability calculated from the 2D segmented image to characterize the rock at the location in the boreholes.

42. The present invention also relates to a system for estimating a target rock property of a rock sample from an application of digital rock physics in 2D, comprising:
(a) an X-ray scanner operable to scan a rock sample to obtain a 2D digital image of the rock sample;
(b) one or more computer systems operable to (i) segment the 2D digital image to produce a digital 2D segmented image having pixels characterized as pore space and pixels characterized as mineral matrix and defining a boundary at the intersection of pore space and the mineral matrix, (ii) derive values for rock properties $P_1$-$P_i$ from the segmented image as a function of simple pore space geometry, (iii) apply a transform relationship adapted for application to a 2D segmented image environment to calculate an estimated value for a target rock property as a function of simple pore space geometry derived from the 2D segmented image, and (iv) output the results to at least one device to display, print, or store results of the computations; and
(c) at least one device to display, print, or store results of the computations.

43. The system of any preceding or following embodiment/feature/aspect, wherein the target rock property is absolute permeability, relative permeability, formation factor, elasticity, or capillary pressure.

44. The present invention also relates to a computer program product on a computer readable medium that, when performed on a processor in a computerized device provides a method for performing computations of one or more or all of the indicated steps of the of the preceding method and system.

The present invention can include any combination of these various features or embodiments above and/or below as set forth in sentences and/or paragraphs. Any combination of disclosed features herein is considered part of the present invention and no limitation is intended with respect to combinable features.

Applicants specifically incorporate the entire contents of all cited references in this disclosure. Further, when an amount or other value or parameter is given as either a range, preferred range, or list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range. Other embodiments of the present invention will be apparent to those skilled in the art form consideration of the present specification and practice of the present invention disclosed herein. It is intended that the present specification and examples be considered as exemplary only with a true scope and spirit of the invention being indicated by the following claims and equivalents thereof.

What is claimed is:

1. A method for estimating a target rock property of a rock sample from an application of digital rock physics in 2D, comprising:
scanning a rock sample to obtain a 2D digital image of the rock sample;
segmenting the digital image to produce a digital 2D segmented image having pixels characterized as pore space and pixels characterized as mineral matrix and defining a boundary at the intersection of pore space and the mineral matrix;
deriving values for rock properties $P_1$-$P_1$ from the segmented image as a function of pore space geometry; and
applying a transform relationship adapted for application to a 2D segmented image environment to calculate an estimated value for a target rock property as a function of pore space geometry derived from the 2D segmented image, wherein the target rock property is absolute permeability, wherein the transform relationship is adapted by deriving a transform that is wholly a function of pore space geometry, and wherein the transform relationship further comprises a Kozeny-Carman equation and adaptation further comprises converting the property of tortuosity to one or more functions of pore space geometry.

2. The method of claim 1, further comprising obtaining a value for one or more properties in a set-up step, said values being suitable for application for at least a class of rocks under investigation and wherein the transform relationship adapted for application to a 2D segmented image environment otherwise applies only values obtained from the 2D segmented image as a function of simple pore space geometry.

3. The method of claim 2,
wherein deriving values for rock properties $P_1$-$P_i$ from the segmented image as a function of pore space geometry comprises obtaining estimates of porosity and specific surface area; and
obtaining a value for one or more properties in a set-up step comprises obtaining a value for percolation porosity $\phi_p$ in set-up for a group of samples, the method of obtaining comprising selecting from a group comprising one or more of: computation through application of a dilation/erosion algorithm to the 2D segmented image, computing the porosity of a region of disconnected pore space in a 3D digital volume of a sample representative of the group, otherwise analyzing a digital data set; and analyzing a related physical data set for the porosity at which absolute permeability becomes zero.

4. The method of claim 3, wherein converting the property of tortuosity to one or more functions of pores space geometry further comprises:
obtaining and calibrating a relationship defining an upper bound for tortuosity as a function of pore space geometry; said relationship comprising:

$$\tau=0.4476(\phi-\phi_p)^{-1.2}$$

obtaining and calibrating a relationship defining a lower bound for tortuosity as a function of pore space geometry; said relationship comprising $$\tau=0.4038(1+(\phi-\phi_p)^{-1}),$$

wherein the Kozeny-Carman equation applied comprises:

$$k=\frac{1}{2}[(\phi-\phi_p)^3/s^2\tau^2)$$

where:
$\phi$ is porosity;
$\phi_p$ is percolation porosity;
s is specific surface area; and
$\tau$ is tortuosity; and
wherein applying a transform relationship adapted for application to a 2D segmented image environment further comprises substituting relationships defining upper and lower bounds for tortuosity into the Kozeny-Carman relationship such that bounds for absolute permeability comprise:

$$k_- = 2.4957 \frac{(\phi - \phi_p)^{5.4}}{s^2}, k_+ = 3.0665 \frac{(\phi - \phi_p)^5}{s^2(1 + \phi - \phi_p)^2}.$$

5. The method of claim 4, wherein the deriving values for rock properties $P_1$-$P_i$ from the 2D segmented image as a function of pore space geometry comprises obtaining estimates of porosity and specific surface area.

6. The method of claim 3, wherein the Kozeny-Carman equation applied comprises:

$$k = \frac{d^2}{72} \frac{(\phi - \phi_p)^3}{[1 - (\phi - \phi_p)]^2 \tau^2},$$

and
wherein deriving values for rock properties $P_1$-$P_i$ from the segmented image as a function of pore space geometry comprises obtaining estimates of porosity, specific surface area, and grain size.

7. The method of claim 3, wherein applying the adapted transform relationship further comprises solving for upper and lower bounds for tortuosity and inserting these computed values into the Kozeny-Carman equation to define estimates for $k_+$ and $k_-$.

8. The method of claim 1, wherein converting the property of tortuosity to one or more functions of pore space geometry further comprises:
obtaining a relationship defining an upper bound for tortuosity as a function of pore space geometry;
obtaining a relationship defining a lower bound for tortuosity as a function of pore space geometry; and
calibrating the relationships defining the upper and lower bounds for tortuosity in
a set-up step.

9. The method of claim 8 wherein:
the relationship defining an upper bound for tortuosity, after calibration, comprises:

$\tau = 0.4476\phi^{-1.2}$ the relationship defining a lower bound for tortuosity, after calibration, comprises:

$\tau = 0.4038(1+\phi^{-1})$, wherein the Kozeny-Carman equation applied comprises:

$$k = \frac{10^9}{2} \frac{\phi^3}{s^2 \tau^2},$$

and
wherein deriving values for rock properties $P_1$-$P_i$ from the segmented image as a function of pore space geometry comprises obtaining estimates of porosity and specific surface area values; and
applying the adapted transform relationship further comprises solving for upper and lower bounds for tortuosity and inserting these computed values into the Kozeny-Carman equation to define estimates for $k_+$ and $k_-$,
wherein applying a transform relationship adapted for application to a 2D segmented image environment further comprises substituting relationships defining upper and lower bounds for tortuosity into the Kozeny-Carman relationship such that bounds for absolute permeability comprise:

$$k_- = 2.4957 \frac{\phi^{5.4}}{s^2}, k_+ = 3.0665 \frac{\phi^5}{s^2(1+\phi)^2}.$$

10. The method of claim 1, wherein the transform relationship adapted for application to a 2D segmented image environment was adapted from an original expression having at least one property which is converted to a function of pore space geometry.

11. The method of claim 1, wherein applying a transform relationship for application to a 2D segmented image environment further comprises using an adaptation of Timur's equation where the parameter of irreducible water saturation is addressed as a function of pore space geometry.

12. The method of claim 11, wherein addressing irreducible water saturation comprises:
using a relationship of irreducible water saturation and properties of pore space geometry selected from a group comprising one or more of grain diameter, specific surface area, or capillary diameter.

13. A method for efficiently characterizing rock traversed while drilling a borehole for hydrocarbon reservoir development with an estimated value for a target rock property that is absolute permeability, comprising:
obtaining a rock sample having a provenance of collection linked to a specific region of the borehole;
scanning the rock sample to obtain a 2D digital image of the rock sample;
segmenting the digital image to produce a 2D segmented image having pixels characterized as pore space and pixels characterized as mineral matrix and defining a boundary at the intersection of pore space and mineral matrix;
applying a transform relationship adapted for direct application to a 2D segmented image environment to calculate the estimated value for a target rock property, which further comprises applying a Kozeny-Carman equation adapted to be limited to variables of pore space geometry for which estimate values for absolute permeability are directly calculated from the 2D segmented image, and adaptation further comprises converting the property of tortuosity to one or more functions of pore space geometry; and
using the estimated value for the target rock property directly derived from the 2D segmented image to characterize the rock at region of the borehole.

14. The method of claim 13, wherein scanning the rock sample to obtain a 2D digital image comprises using one or more scanning systems selected from a group comprising:

focused ion beam scanning electron microscope; x-ray tomography; synchrotron, microtomography, and microradiology.

15. The method of claim 13, wherein applying the adapted Kozeny-Carman equation further comprises:
estimating a minimum value for absolute permeability $k_-$ based on the relationship:

$$k_-=2.4957(\phi^{5.4}/s^2)$$

where porosity $\phi$ is estimated as the number of pore space pixels divided by the total number of pixels in the 2D segmented image; and specific surface area s is estimated as the length of the boundary at the intersection of the pore space and the solid matrix divided by the area of the 2D segmented image.

16. The method of claim 15 wherein applying the adapted Kozeny-Carman equation further comprises:
bounding the estimated value for absolute permeability k between the estimated minimum $k_-$ and an estimated maximum $k_+$; and
estimating the maximum value for absolute permeability $k_+$ based on the relationship:

$$k_+=3.0665[\phi^5/s^2(1+\phi)^2], \text{ and}$$

bounding the estimated value for absolute permeability k between the estimated minimum $k_-$ and an estimated maximum $k_+$.

17. The method of claim 13, wherein using the calculated estimate value for the target rock property directly derived from the 2D segmented image to characterize the rock comprises sampling at multiple locations throughout a zone of interest to produce estimates with a continuity useful for defining the boundaries of a zone of interest in a time frame useful for the drilling program.

18. The method of claim 13, wherein using the estimated value of the target rock property directly derived from the 2D segmented image to characterize the rock comprises sampling and making estimates substantially continuously to augment logging while drilling (LWD) data to facilitate understanding a length along the borehole.

19. The method of claim 13 wherein:
obtaining the rock sample comprises using rock samples collected from drill cuttings in the ordinary course of drilling and associating the drill cutting to an axial depth in the borehole as a function of time to appearance at the surface and
using the estimated value for the target rock property directly derived from the 2D segmented image to characterize the rock comprises sampling at multiple locations throughout a zone of interest to produce estimates with a continuity useful for defining the boundaries of a zone.

20. The method of claim 13, wherein using the estimated value for the target rock property derived from the 2D segmented image to characterize the rock comprises sampling and making estimates nearly continuously to augment logging while drilling (LWD) data to facilitate understanding the rock across an interval in the borehole.

21. A method for efficiently characterizing rock traversed while drilling a borehole for hydrocarbon reservoir development with an estimated an estimated absolute permeability value k, comprising:
obtaining a rock sample having a provenance of collection linked to a specific region of the borehole;
scanning the rock sample to obtain a 2D digital image of the rock sample, said scanning comprising using one or more scanning systems of a group comprising: focused ion beam scanning electron microscope; x-ray tomography; synchrotron, microtomography, and microradiology;
segmenting the digital image to produce a 2D segmented image having pixels characterized as pore space and pixels characterized as solid matrix and defining a boundary at the intersection of pore space and solid matrix;
applying a Kozeny-Carman equation adapted for direct application to a 2D segmented image environment with which an estimate is directly calculated from the 2D segmented image for absolute permeability, and adaptation further comprises converting the property of tortuosity to one or more functions of pore space geometry; and
using the estimate for absolute permeability calculated from the 2D segmented image to characterize the rock at said location in the borehole.

22. The method of claim 21, wherein:
applying the Kozeny-Carman equation adapted for direct application to a 2D segmented image environment further comprises:
applying the Kozeny-Carman equation adapted from:

$$k=\tfrac{1}{2}(\phi^3/s^2\tau^2)$$

where:
$\phi$ is porosity;
s is specific surface area; and
$\tau$ is tortuosity; and
tortuosity $\tau$ is replaced with a relation that is a function of porosity $\phi$ and specific surface area s derived through means comprising one or more of a group comprising empirical transform, theoretical physics, and calibration techniques;
estimating porosity $\phi$ as the number of pore space pixels divided by the total number of pixels in the 2D segmented image; and
estimating specific surface area s as the length of the boundary at the intersection of pore space and solid matrix divided by the area of the 2D segmented image, and
wherein applying the adapted Kozeny-Carman equation further comprises estimating absolute permeability by defining lower and upper boundaries, comprising:
using a first tortuosity relationship $\tau=0.4476\phi-1.2$ in estimating a lower bound for absolute permeability $k_-$ according to the following relationship:

$$k_-=2.4957(\phi^{5.4}/s^2), \text{ and}$$

using a second tortuosity relationship $\tau=0.40381(1+\phi^{-1})/2$ in
estimating an upper bound for absolute permeability $k_+$ according to the following relationship:

$$k_+=3.0665[\phi^5/s_2(1+\phi)^2].$$

23. The method of claim 21, wherein:
applying the Kozeny-Carman equation adapted for direct application to a 2D segmented image environment further comprises:
applying the Kozeny-Carman equation adapted from:

$$k=\tfrac{1}{2}[(\phi-\phi_p)^3/s^2\tau^2)$$

where:
$\phi$ is porosity;
$\phi_p$ is percolation porosity;
s is specific surface area; and
$\tau$ is tortuosity; and
tortuosity $\tau$ is replaced with a relation that is a function of porosity $\phi$ and specific surface area s derived through means comprising one or more of a group comprising empirical transform, theoretical physics, and calibration techniques;
estimating porosity $\phi$ as the number of pore space pixels divided by the total number of pixels in the 2D segmented image; and
estimating specific surface area s as the length of the boundary at the intersection of pore space and solid matrix divided by the area of the 2D segmented image.

24. The method of claim 23 wherein applying the adapted Kozeny-Carman equation further comprises:
using a first tortuosity relationship $\tau = 0.4476(\phi-\phi_p)^{-1.2}$ in estimating a lower bound for absolute permeability $k_-$ according to the following relationship:

$$k_- = 2.4957[(\phi-\phi_p)^{5.4}/s^2].$$

25. The method of claim 24 wherein applying the adapted Kozeny-Carman equation further comprises estimating absolute permeability by defining lower and upper boundaries, and further comprising:
using a second tortuosity relationship $\tau = 0.40381(1+(\phi-\phi_p)^{-1})/2$ in
estimating an upper bound for absolute permeability $k_+$ according to the following relationship:

$$k_+ = 3.0665[(\phi-\phi_p)^5/s^2(1+\phi-\phi_p)^2].$$

26. The method of claim 21, wherein:
applying the Kozeny-Carman equation adapted for direct application to a 2D segmented image environment further comprises:
applying the Kozeny-Carman equation adapted from:

$$k = d^2(\phi-\phi_p)^3/72[1-(\phi-\phi_p)]^2\tau^2)$$

where:
$\phi$ is porosity;
$\phi_p$ is percolation porosity;
d is grain diameter;
s is specific surface area; and
$\tau$ is tortuosity; and
tortuosity $\tau$ is replaced with a relation that is a function of porosity $\phi$ and specific surface area s derived through means comprising one or more of a group comprising empirical transform, theoretical physics, and calibration techniques;
estimating porosity $\phi$ as the number of pore space pixels divided by the total number of pixels in the 2D segmented image; and
estimating specific surface area s as the length of the boundary at the intersection of pore space and solid matrix divided by the area of the 2D segmented image.

27. A system for estimating a target rock property of a rock sample from an application of digital rock physics in 2D, comprising:
(a) an X-ray scanner operable to scan a rock sample to obtain a 2D image of the rock sample;
(b) one or more computer systems operable to (i) segment the 2D digital image to produce a digital 2D segmented image having pixels characterized as pore space and pixels characterized as mineral matrix and defining a boundary at the intersection of pore space and the mineral matrix, (ii) derive values for rock properties $P_1$-$P_i$ from the segmented image as a function of pore space geometry, (iii) apply a transform relationship adapted for application to a 2D segmented image environment to calculate an estimated value for a target rock property as a function of pore space geometry derived from the 2D segmented image, wherein the target rock property is absolute permeability, wherein the transform relationship is adapted by deriving a transform that is wholly a function of pore space geometry, and wherein the transform relationship further comprises a Kozeny-Carman equation and adaptation further comprises converting the property of tortuosity to one or more functions of pore space geometry, and (iv) output the results to at least one device to display, print, or store results of the computations; and
(c) at least one device to display, print, or store results of the computations.

28. A non-transitory computer-readable storage medium and a computer program product stored on the storage medium that, when performed on a processor in a computerized device provides a method for performing computations of one or more or all of the indicated steps of the method of claim 1.

* * * * *

UNITED STATES PATENT AND TRADEMARK OFFICE
CERTIFICATE OF CORRECTION

PATENT NO. : 9,046,509 B2  
APPLICATION NO. : 13/895454  
DATED : June 2, 2015  
INVENTOR(S) : Dvorkin et al.

Page 1 of 1

It is certified that error appears in the above-identified patent and that said Letters Patent is hereby corrected as shown below:

IN THE CLAIMS:

Claim 1, column 28, line 17, "$P_1- P_1$" should read --$P_1-P_i$--;

Claim 9, column 30, line 10, "relationshipadapted" should read --relationship adapted--;

Claim 21, column 31, line 62, "with an estimated an estimated absolute" should read --with an estimated absolute--; and Claim 22, column 32, line 48, "$\tau=0.4476\phi-1.2$" should read --$\tau=0.4476\phi^{-1.2}$--.

Signed and Sealed this  
Twenty-ninth Day of September, 2015

Michelle K. Lee  
*Director of the United States Patent and Trademark Office*